United States Patent
Kovatchev et al.

(10) Patent No.: US 9,398,869 B2
(45) Date of Patent: Jul. 26, 2016

(54) METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES

(75) Inventors: Boris P. Kovatchev, Charlottesville, VA (US); Marc D. Breton, Charlottesville, VA (US); Stephen D. Patek, Charlottesville, VA (US); Colleen Hughes Karvetski, Charlottesville, VA (US)

(73) Assignee: University of Virginia Patent Foundation, Charlottesville, VA (US)

( * ) Notice: Subject to any disclaimer, the term of this patent is extended or adjusted under 35 U.S.C. 154(b) by 821 days.

(21) Appl. No.: 13/637,359

(22) PCT Filed: Mar. 24, 2011

(86) PCT No.: PCT/US2011/029793
§ 371 (c)(1),
(2), (4) Date: Dec. 10, 2012

(87) PCT Pub. No.: WO2011/119832
PCT Pub. Date: Sep. 29, 2011

(65) Prior Publication Data
US 2013/0079613 A1      Mar. 28, 2013

Related U.S. Application Data

(60) Provisional application No. 61/317,902, filed on Mar. 26, 2010.

(51) Int. Cl.
- A61B 5/00 (2006.01)
- A61B 5/145 (2006.01)
- A61B 5/1495 (2006.01)
- A61M 1/36 (2006.01)
- A61M 5/142 (2006.01)

(52) U.S. Cl.
CPC ........... *A61B 5/14532* (2013.01); *A61B 5/1495* (2013.01); *A61B 5/4839* (2013.01); *A61B 5/725* (2013.01); *A61B 5/7225* (2013.01); *A61M 1/36* (2013.01); *A61M 5/142* (2013.01); *A61B 2560/0223* (2013.01)

(58) Field of Classification Search
None
See application file for complete search history.

(56) References Cited

U.S. PATENT DOCUMENTS

| | | | | |
|---|---|---|---|---|
| 2002/0099282 | A1* | 7/2002 | Knobbe et al. | 600/365 |
| 2004/0133081 | A1* | 7/2004 | Teller et al. | 600/300 |

(Continued)

FOREIGN PATENT DOCUMENTS

WO    2010025431 A1    3/2010

*Primary Examiner* — Etsub Berhanu
(74) *Attorney, Agent, or Firm* — Vorys, Sater, Seymour and Pease LLP; Vincent M DeLuca; Robert J. Decker

(57) ABSTRACT

Method and System for providing a signal from an insulin pump, artificial pancreas, or another insulin delivery device as a source of information for improving the accuracy of a continuous glucose sensor (CGS). The effect of using insulin information to enhance sensor accuracy is most prominent at low blood glucose levels, i.e. in the hypoglycemic range, which is critical for any treatment. A system for providing a filtering/state estimation methodology that may be used to determine a glucose state estimate at time t-τ. The estimation may be extrapolated to some future time t and then the extrapolated value is used to extract the blood glucose component. The blood glucose component of the extrapolation and the output of the CGS are weighted and used to estimate the blood glucose level of a subject.

90 Claims, 10 Drawing Sheets

(56) References Cited

U.S. PATENT DOCUMENTS

| | | |
|---|---|---|
| 2008/0314395 A1 | 12/2008 | Kovatchev et al. |
| 2009/0055149 A1 | 2/2009 | Hayter et al. |
| 2009/0171589 A1 | 7/2009 | Kovatchev |
| 2011/0237917 A1* | 9/2011 | Roy et al. ............ 600/365 |

* cited by examiner

| All data: % A-zone of the CG-EGA | Hypoglycemia (BG<=70 mg/dl) | | Euglycemia (70<BG<=180 mg/dl) | | Hyperglycemia (BG>180 mg/dl) | |
|---|---|---|---|---|---|---|
| | Insulin-enhanced accuracy | Raw CGS accuracy | Insulin-enhanced accuracy | Raw CGS accuracy | Insulin-enhanced accuracy | Raw CGS accuracy |
| No weighing | 95.0% | 83.5% | 97.5% | 95.4% | 97.2% | 95.5% |
| LBGI-based weighting | 95.1% | 83.5% | 95.0% | 95.4% | 95.8% | 95.5% |

Figure 6

| All data: % A-zone of the EGA | Insulin-enhanced accuracy | Raw CGS accuracy |
|---|---|---|
| Insulin-Bolus Based Weighting | 93.55 | 83.87 |

Figure 8

| All data: % A-zone of the EGA | Insulin-enhanced accuracy | Raw CGS accuracy |
|---|---|---|
| Insulin-Bolus Based Weighting | 70.25 | 64.86 |

METHOD, SYSTEM, AND COMPUTER PROGRAM PRODUCT FOR IMPROVING THE ACCURACY OF GLUCOSE SENSORS USING INSULIN DELIVERY OBSERVATION IN DIABETES

RELATED APPLICATIONS

The present application is a national stage filing of International Application No. PCT/US2011/029793, filed Mar. 24, 2011, which claims priority under 35 U.S.C. §119(e) from U.S. Provisional Application Ser. No. 61/317,902 filed Mar. 26, 2010, entitled "Method, System and Computer Program Product for Improving the Accuracy of Continuous Glucose Sensors Using Insulin Delivery Observation in Diabetes;" the disclosures of which are hereby incorporated by reference herein in their entirety.

FIELD OF INVENTION

The present invention relates generally to the field of medical devices to be used as glucose sensors. More specifically, the invention is in the subfield of glucose sensors and other tools to be used for monitoring glucose levels of a subject.

BACKGROUND OF THE INVENTION

Continuous glucose sensors offer the potential to markedly change our understanding of glucose homeostasis in health and disease, and to provide the missing information required to achieve near-normoglycemia among persons with both Type 1 and Type 2 diabetes. Despite their having appeared on the scene less than five years ago, continuous glucose sensors (CGS) already have been shown to be associated with short term reductions in glucose variability, time spent in nocturnal hypoglycemia, time spent in hyperglycemia, and lower glycosylated hemoglobin values. Their potential to assist patients and their families in day-to-day decision-making, to warn of impending hypoglycemia and to reduce the fear of its occurrence has yet to be fully appreciated. Indeed, the advent of CGS has stimulated the diabetes research community to re-examine the feasibility of developing a closed loop "artificial pancreas" and preliminary clinical studies of prototype closed loop systems are currently being initiated. Given the enormous therapeutic and safety potential of these systems, it seems reasonable to assume that to some extent they have been proven to be numerically and clinically accurate in both the display of glucose values and the tracking of glucose trends and rate of change.

However, unfortunately, the data regarding the accuracy of different CGS systems is presented according to criteria identical to those developed decades ago for assessing the accuracy of home blood glucose (BG) monitors providing episodic self-monitoring (SBGM) readings, and thus do not include assessments designed to evaluate the "continuous" time-dependent information (in particular rate and direction of glucose change), which is unique to CGS. Regardless of the criteria used, sensor accuracy is still substantially inferior to the accuracy of self-monitoring devices that use capillary blood (finger sticks) for glucose determination. This inaccuracy is primarily evident during hypoglycemia and is due to delays observed during blood-to-interstitial glucose transport and other factors.

BRIEF SUMMARY OF INVENTION

The common denominator for all accuracy-enhancing procedures reviewed in the previous section is that they rely on blood glucose data only (e.g. raw sensor current, calibration points, etc.). However, the field is rapidly moving toward systems combining continuous glucose sensors (CGS) with insulin pump, such as the new Medtronic Paradigm RT devices. Thus, insulin delivery data will become available to the sensor processor.

An aspect of an embodiment of the present invention focuses, for the first time, on the signal from an insulin pump, artificial pancreas, or another insulin delivery device as a source of information for improvement of the accuracy of the CGS that is coupled with an insulin pump, artificial pancreas, or another insulin delivery device. As seen from the simulation results included in the following section, the effect of using insulin information to enhance sensor accuracy is most prominent at low blood glucose levels (where the sensor has been shown to be the most inaccurate), i.e., in the hypoglycemic range, which is critical for any treatment.

Another aspect of an embodiment of the invention is the use of a filtering/state estimation procedure, such as a Kalman Filter methodology, H-infinity filtering method, a Bayesian filtering method, a Monte Carlo method, or a least squares method, to determine a metabolic state estimate, of which the blood glucose state is a component, at time t-τ.

Another aspect of an embodiment of the invention is the use of the metabolic state estimate at time t-τ to infer the metabolic state estimate at time t given the metabolic state estimate and insulin information up to time t-τ.

Another aspect of an embodiment of the invention is the extraction of the blood glucose component from the metabolic state estimate.

Another aspect of an embodiment of the invention is the use of a weighting scheme to weight the information from the CGS and the blood glucose component of the metabolic state estimate. The weights can be determined in many ways. In one embodiment of the invention, more weight is given to the KF glucose estimate during hypoglycemia and more weight is given to the CGS reading during euglycemia and hyperglycemia in accordance with the low BG index.

Many other weighting schemes are possible as well. In another embodiment of the invention, an S-shaped curve increasing at approximately the threshold of hypoglycemia as well as other weighting schemes can be used.

In another embodiment of the invention the weighting scheme accounts directly for the lack of accuracy of the Kalman Filter state estimate immediately following meals and meal insulin boluses. In the time immediately following meals, the CGS measurement is generally more accurate than the Kalman Filter state estimate, since the model at the core of the state estimation procedure does not assume knowledge of meal timing and meal amounts. To account for this, we have developed a weighting scheme that places more weight on the CGS measurement signal in the time following the detection of a large bolus of insulin that is typically associated with a meal.

Another aspect of an embodiment of the invention is a processor configured to perform the required calculations, wherein the processor can be implemented in the CGS, the device providing the insulin, or in a separate device (or implemented integrally among two or more of the CGS, insulin device or a separate device).

An aspect of an embodiment of the present invention provides a method for improving the accuracy of a glucose measurement device. The method may comprise: using insulin delivery information to improve the accuracy of the glucose measurement device.

An aspect of an embodiment of the present invention provides a system for improving the accuracy of a glucose measurement device. The glucose measurement device may use insulin delivery information to improve the accuracy of the glucose measurement device.

An aspect of an embodiment of the present invention provides a computer program product comprising a computer useable medium having a computer program logic for enabling at least one processor in a computer system for improving the accuracy of a glucose measurement device. The computer program logic may comprise: using insulin delivery information or data to improve the accuracy of the glucose measurement device.

It should be appreciated that as discussed herein, a subject may be a human or any animal. It should be appreciated that an animal may be a variety of any applicable type, including, but not limited thereto, mammal, veterinarian animal, livestock animal or pet type animal, etc. As an example, the animal may be a laboratory animal specifically selected to have certain characteristics similar to human (e.g. rat, dog, pig, monkey), etc. It should be appreciated that the subject may be any applicable human patient, for example. Use of the term "patient" to describe various subjects herein below should be understood to be exemplary only. It should be understood that the systems and method discussed can apply to any subject.

These and other objects, along with advantages and features of various aspects of embodiments of the invention disclosed herein, will be made more apparent from the description, drawings and claims that follow.

BRIEF DESCRIPTION OF THE DRAWINGS

The foregoing and other objects, features and advantages of the present invention, as well as the invention itself, will be more fully understood from the following description of the embodiments, when read together with the accompanying drawings.

The accompanying drawings, which are incorporated into and form a part of the instant specification, illustrate several aspects and embodiments of the present invention and, together with the description herein, serve to explain the principles of the invention. The drawings are provided only for the purpose of illustrating select embodiments of the invention and are not to be construed as limiting the invention.

FIG. 6 is a table that shows the improvement in sensor accuracy when insulin delivery data is used.

FIG. 8 is a table that shows the improvement in sensor accuracy when insulin delivery data is used for real CGS measurements and insulin delivery data with regard to the trial in FIG. 7.

FIG. 10 is a table that shows the improvement in sensor accuracy when insulin delivery data is used for real CGS measurements and insulin delivery data with regard to the trial in FIG. 9.

DETAILED DESCRIPTION OF EXEMPLARY EMBODIMENTS OF THE INVENTION

An aspect of an embodiment of the present invention method provides, but not limited thereto, the following steps:

Step 1: Glucose state estimation that uses CGS readings, insulin delivery data from an insulin pump, artificial pancreas, or another insulin delivery device, and Kalman Filter (KF) methodology to estimate the glycemic state of the person;

Step 2: BG prediction and projection of glucose fluctuations a few (e.g. 10; or may be greater or lesser as desired or required) minutes ahead;

Step 3: Weighting of the glucose state estimate against the sensor readings and calculation of a weighted BG estimate.

Figure 1:
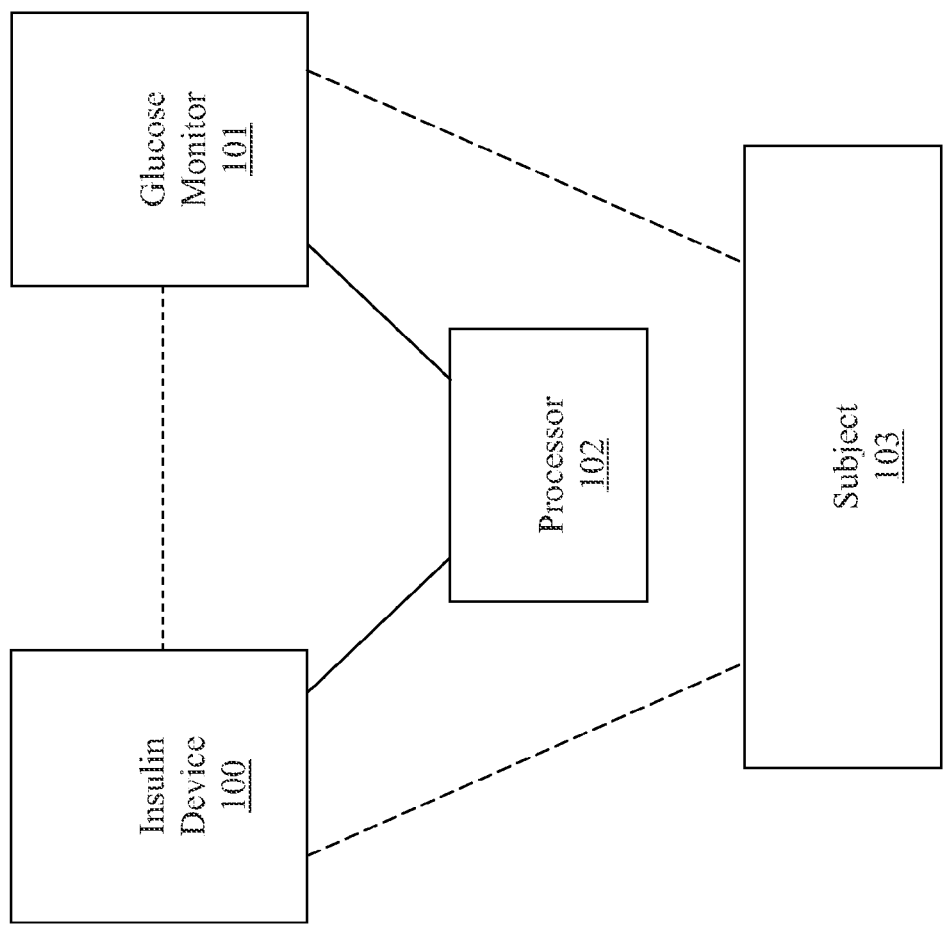
FIG. 1 is a high level functional block diagram of an embodiment of the invention.
Figure 2:
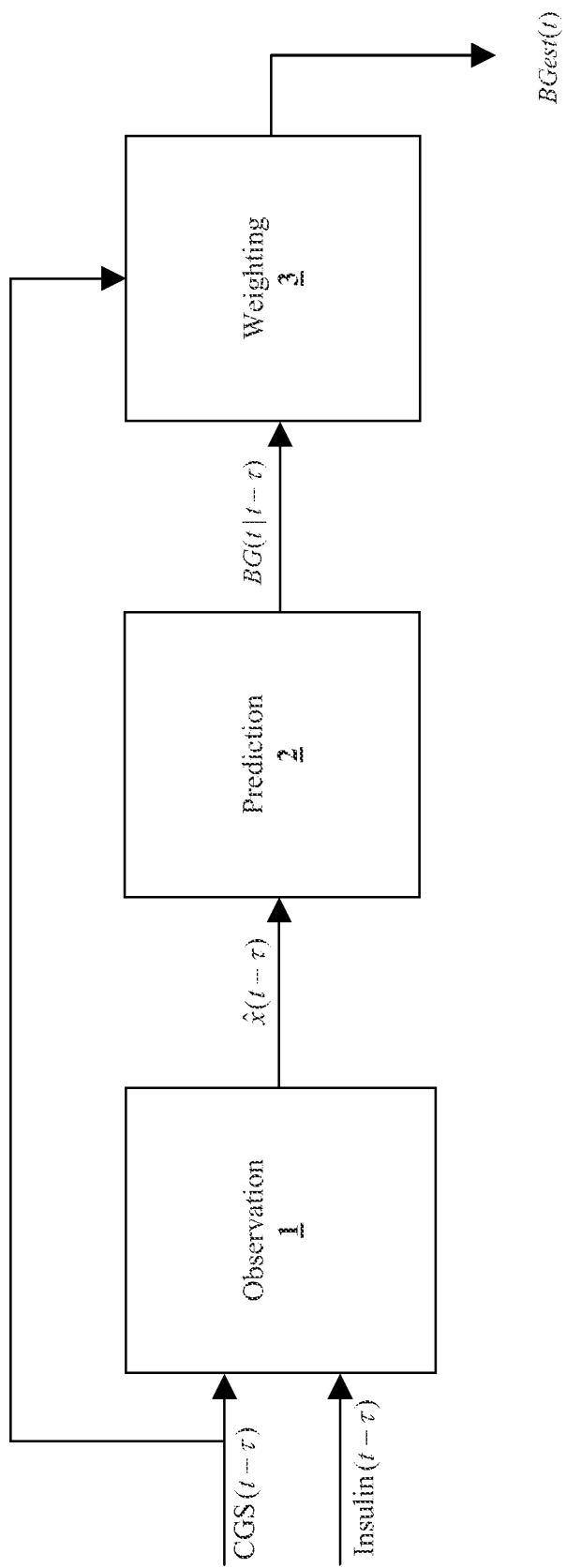
FIG. 2 is a block diagram of the steps taken in an embodiment of the invention to improve the CGS reading using insulin data.

As shown in FIG. 2, the observation 1 refers to step 1, the prediction 2 refers to step 2, and the weighting 3 refers to step 3. As shown in FIG. 1, a processor 102 communicates with the glucose monitor 101 and the insulin device 100. The glucose monitor 101 and the insulin device 100 communicate with the subject 103 to monitor glucose levels of the subject 103 and delivery insulin to the subject 103, respectively. The processor 102 is configured to perform the required calculations. The glucose monitor 101 and the insulin device 100 may be implemented as a separate device or as a single device. The processor 102 can be implemented locally in the glucose monitor 101, the insulin device 100, or a standalone device (or in any combination of two or more of the glucose monitor, insulin device, or a stand along device). The processor 102 or a portion of the system can be located remotely such that the device is operated as a telemedicine device.

Step 1: The Metabolic State Observer and Prediction Module works as follows: Predictions are derived from a state space model of glucose-insulin interactions, as characterized by a vector of metabolic states including both insulin and glucose states in various compartments of the body. The state space model allows for predictions of metabolic states in the future. Since interstitial glucose concentration measurable via CGS are subject to sensor noise and some states of x(t) are not measurable, it is impossible to have perfect knowledge of the state vector x(t), making it necessary to compute an estimate $\hat{x}(t)$ of x(t) based on all available information: (1) delivered insulin $J_{ctrl}(t)$ and (2) CGS measurements of interstitial glucose concentration CGS(t). This is shown as observation 1 in FIG. 2. The CGS measurements of interstitial glucose concentration CGS(t) include readouts that come at certain intervals. The interval can be 60 minutes, 30 minutes, 15 minutes, or anything in between, above, or below. It should be appreciated that intervals may vary and can be omitted as desired or required.

The following subsections present (Step 1.1) the state space model, which can be Kalman Filter methodology, H-infinity filtering method, a Bayesian filtering method, a Monte Carlo method, or a least squares method, from which BG values are predicted, (Step 1.2) the first intermediary computation which includes an algorithmic module responsible for computing state vector estimates $\hat{x}(t)$, which we refer to as the "metabolic state estimate." The output of the first intermediary computation is $\hat{x}(t-\tau)$.

Step 1.1: Glucose State Estimate Based on the Following State Space Model:

All predictions of BG are derived from a population-average model for glucose-insulin kinetics, as described by the vector difference equation:

$$x(t)=Ax(t-1)+Bu(t-1)+G\omega(t-1)$$

where:

1. $x(t)=(\partial G(t)\partial X(t)\partial I_{sc1}(t)\partial I_{sc2}(t)\partial I_p(t)\partial G_{sc}(t)\partial Q_1(t)\partial Q_2(t))^T$ is a vector of state variables referring to:
   a. blood glucose: $\partial G(t)=G(t)-G_{ref}$, where $G(t)$ (mg/dl) is blood glucose concentration at minute t and $G_{ref}=112.5$ (mg/dl) is a reference value for BG
   b. remote compartment insulin action: $\partial X(t)=X(t)-X_{ref}$ where $X(t)$ (min$^{-1}$) represents the action of insulin in the "remote" compartment and $X_{ref}=0$(min$^{-1}$) is a reference value
   c. interstitial insulin, first compartment: $\partial I_{sc1}(t)=I_{sc1}(t)-I_{sc1,ref}$ where $I_{sc1}(t)$ (mU) is insulin stored in the first of two interstitial compartments and $I_{sc1,ref}=1.2949\times10^3$ (mU) is a reference value
   d. interstitial insulin, second compartment: $\partial I_{sc2}(t)=I_{sc2}(t)-I_{sc2,ref}$ where $I_{sc2}(t)$ (mU) is insulin stored in the second of two interstitial compartments and $I_{sc2,ref}=1.2949\times10^3$ (mU) is a reference value
   e. plasma insulin: $\partial I_p(t)=I_p(t)-I_{p,ref}$ where $I_p(t)$ (mU) is plasma insulin and $I_{p,ref}=111.2009$ (mU) is a reference value
   f. interstitial glucose concentration: $\partial G_{sc}(t)=G_{sc}(t)-G_{sc,ref}$ where $G_{sc}(t)$ (mg/dl) is the concentration of glucose in interstitial fluids, and $G_{sc,ref}=112.5$ (mg/dl) is a reference value
   g. gut compartment 1: $\partial Q_1(t)=Q_1(t)-Q_{1,ref}$ where $Q_1(t)$ (mg) is glucose stored in the first of two gut compartments and $Q_{1,ref}=0$ (mg) is a reference value
   h. gut compartment 2: $\partial Q_2(t)=Q_2(t)-Q_{2,ref}$ where $Q_2(t)$ (mg) is glucose stored in the second of two gut compartments and $Q_{2,ref}=0$ (mg) is a reference value
2. $u(t)=J_{ctrl}(t)-J_{basal}(t)$ (mU/min) is the insulin control signal at time t, where $J_{ctrl}(t)$ (mU/min) is the current rate of insulin infusion and $J_{basal}(t)$ (mU/min) is the patient's normal basal rate
3. $\omega(t)=$meal$(t)-$meal$_{ref}$ (mg/min) is the ingested glucose disturbance signal at time t, where meal(t) is the rate of glucose ingestion and meal$_{ref}=0$ (mg/min) is a reference meal input value
4. the state space matrices A, B, and G are Step 1.2: Glucose State Estimate is then Produced as Follows:

To compute estimates $\hat{x}(t)$ of $x(t)$ we use knowledge of infused insulin $u(t)$ and measurements $y(t)=CGS(t)-G_{ref}$ (mg/dl), where CGS(t) is the readout of the CGS at time t. We model the measurement signal from CGS(t) as $$y(t)=Cx(t)+v(t)$$

where:
1. $v(t)$ (mg/dl) represents CGS signal noise
2. the state space matrix C is $$C^T=[1\ 0\ 0\ 0\ 0\ 0\ 0\ 0]$$

The metabolic state observer is derived from the state space model for $x(t)$ and $y(t)$ as a Kalman filter, treating a possible meal disturbance process $\omega(t)$ and the noise process $v(t)$ as zero-mean, white, Gaussian processes with covariances $R=k_1=1$ and $Q=k_2=0.0025$, respectively. (We point out that, even though meals $\omega(t)$ and sensor noise $v(t)$ are not zero-mean, white, Guassian processes in reality, the resulting Kalman filter is still a stable state observer.) The observer itself can be expressed recursively (as a dynamic process) as $$\hat{x}(t+1|t)=A\hat{x}(t|t-1)+Bu(t)+L(y(t)-C\hat{x}(t|t-1))$$

$$\hat{x}(t)=\hat{x}(t|t-1)+M(y(t)-C\hat{x}(t|t-1)),$$

where:
1. $\hat{x}(t|t-1)$ refers to the best estimate of $x(t)$ using data collected up to stage $t-1$
2. $\hat{x}(t)$ refers to the best estimate of $x(t)$ using data collected up to stage t
3. the filter gain matrix $L=APC^T(CPC^T+R)^{-1}$
4. the estimate update matrix $M=PC^T(CPC^T+R)^{-1}$
5. the matrix P is the unique stabilizing solution to the algebraic Riccati equation:

$$A^TPA-A^TPG(G^TPG+R)^{-1}G^TPA+Q=P$$

Step 2: BG Prediction

A second intermediary computation is performed. This prediction 2 as shown in FIG. 2 uses the output of the first intermediary computation to predict the output of the second intermediary computation. The output of the second intermediary computation is BG(t|t-$\tau$). Predictions are derived from the latest estimate of the metabolic state of the patient $\hat{x}(t-\tau)$ extrapolated to some future time t (where we can think of $\tau$ as the time lag, in minutes, associated with the CGS signal because while the CGS signal is a measurement at time t, the actual output of CGS represents a measurement at time $t-\tau$), assuming that all inputs are held at their steady state values:

$$\hat{x}(t|t-\tau)=A^\tau\hat{x}(t-\tau)+A(\tau)Bu(t-\tau)+A(\tau)G\omega(t-\tau),$$

$$A = \begin{bmatrix} .9913 & -102.7 & -1.50\times10^{-8} & -2.89\times10^{-6} & -4.1\times10^{-4} & 0 & 2.01\times10^{-6} & 4.30\times10^{-5} \\ 0 & .839 & 5.23\times10^{-10} & 7.44\times10^{-8} & 6.84\times10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9\times10^{-4} & .0180 & .7882 & 0 & 0 & 0 \\ .0865 & -4.667 & -2.73\times10^{-10} & -6.59\times10^{-8} & -1.26\times10^{-5} & .9131 & 6.00\times10^{-8} & 1.90\times10^{-6} \\ 0 & 0 & 0 & 0 & 0 & 0 & .9083 & 0 \\ 0 & 0 & 0 & 0 & 0 & 0 & .09115 & .9891 \end{bmatrix}$$

$$B^T = [\ -3.05\times10^{-9}\ \ 1.34\times10^{-10}\ \ .9900\ \ .0100\ \ 6.50\times10^{-5}\ \ -4.61\times10^{-11}\ \ 0\ \ 0\ ]$$

$$G^T = [\ 6.76\times10^{-7}\ \ 0\ \ 0\ \ 0\ \ 0\ \ 1.52\times10^{-8}\ \ .9534\ \ 0.0464\ ]$$

where:
1. $\hat{x}(t|t-\tau)$ refers to the prediction of $x(t)$ given data up to time $t-\tau$
2. $A^\tau = A \cdot A \ldots A$, i.e. the $\tau$-fold composition of $A$
3. $A(\tau) = \Sigma_{s=0}^{\tau-1} A^s$, with $A(0) = 0_{8 \times 8}$.

In our software implementation, $A^\tau$ and $A(\tau)$ are pre-computed prior to run-time up to the largest necessary prediction horizon. Predicted BG $\tau$ minutes from the current time $t$ is computed as:

$$BG(t|t-\tau) = C\hat{x}(t|t-\tau).$$

Figure 3:
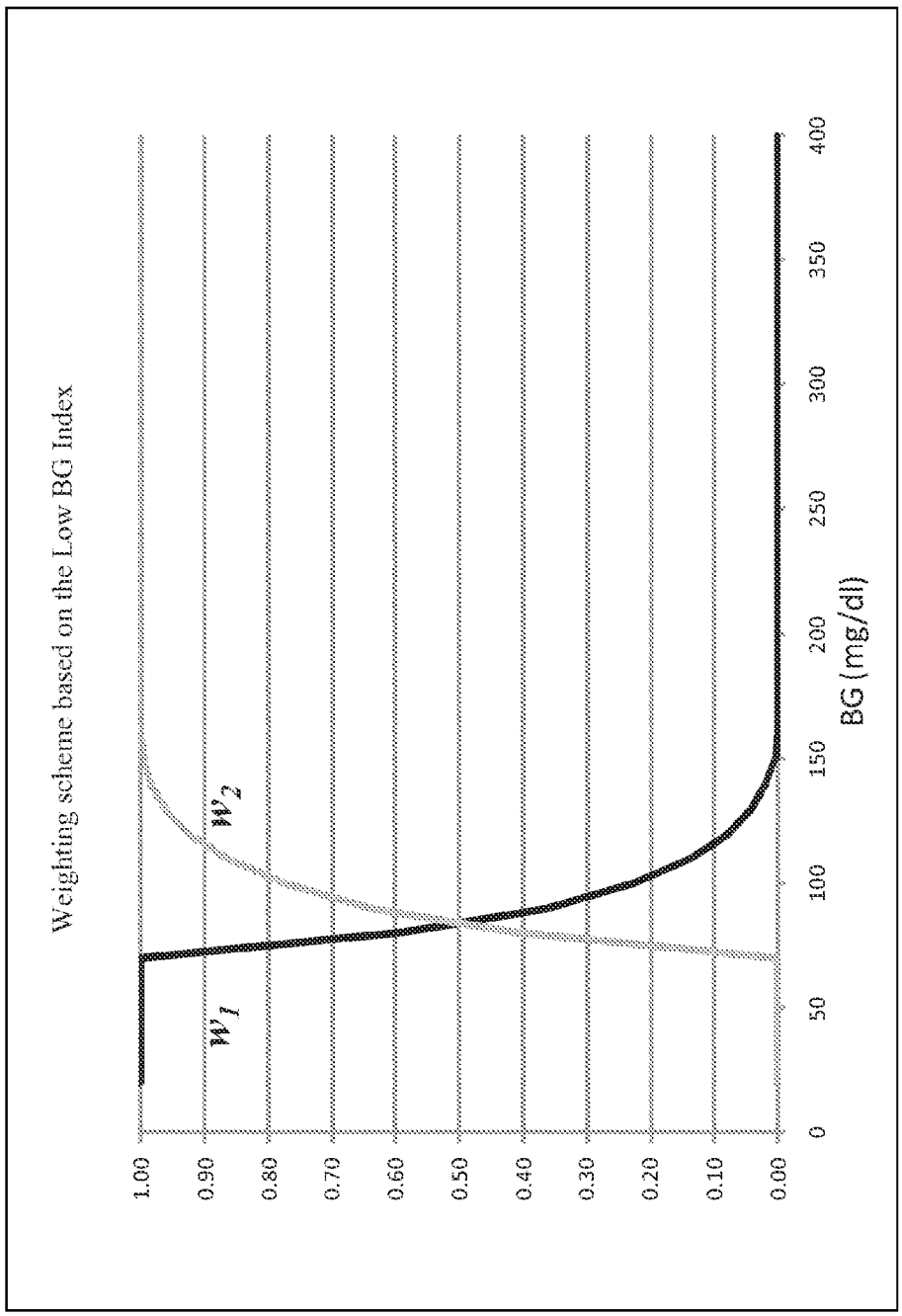
FIG. 3 graphically shows the weighting scheme based on the Low BG Index.
Figure 4:
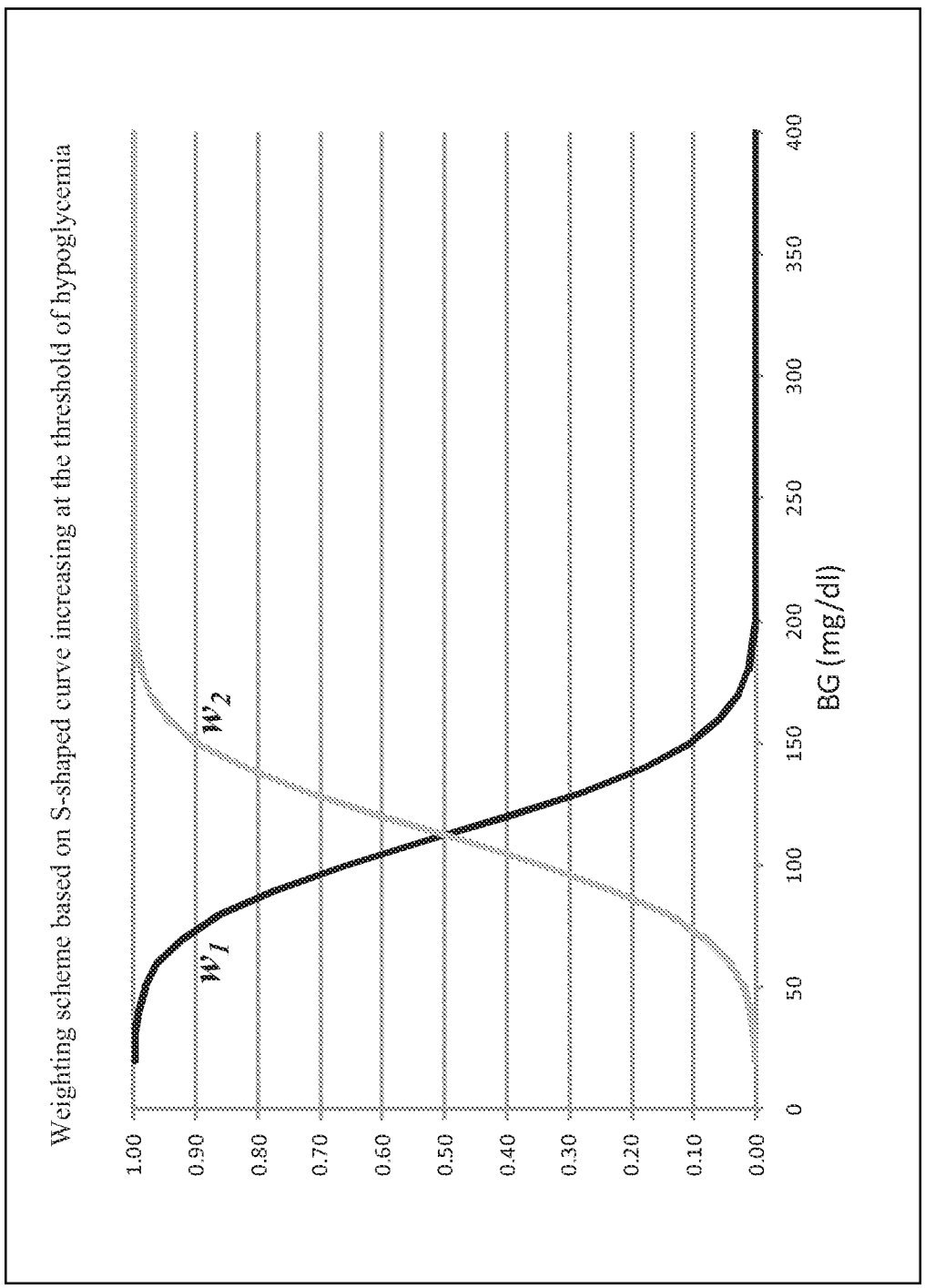
FIG. 4 graphically shows the weighting scheme based on S-shaped curve increasing at the threshold of hypoglycemia.

Step 3: The weighting of glucose state estimates against the sensor readings works as follows: First, each CGS reading (e.g. CGS readings retrieved every 5, 10, 15, 30, 45, or 60 minutes; or may be lesser than or greater than as desired or required, as well as some readings omitted and intervals vary as desired or required) is coupled with insulin data from the pump and is converted into $\hat{x}(t)$ as described above. The final BG determination is then given by the formula:

$$BGest(t) = w_1 \cdot BG(t|t-\tau) + w_2 \cdot CGS(t)$$

Where $w_1$ and $w_2$ are weights assigned to the KF estimate and raw CGS data, respectively, with $w_1 + w_2 = 1$. The weights $w_1$ and $w_2$ can be determined in many ways, but the general rule is that more weight is given to the KF estimate during hypoglycemia (e.g. $w_1 \approx 1$ during progressive hypoglycemia) and more weight is given to the CGS reading during euglycemia and hyperglycemia (e.g. $w_2 \approx 1$ during progressive hyperglycemia). One implementation of a weighting scheme is presented in FIG. 3. The weights in this case are given by the formula: $w_1 = LBGI(CGS-50)/100$ where $LBGI(x)$ is the previously introduced low BG index [28]. Many other weightings are possible as well. As shown in FIG. 4, an S-shaped curve increasing at approximately the threshold of hypoglycemia as well as other weighting schemes can be used.

Another implementation for weights $w_1$ and $w_2$ is one that accounts directly for the lack of accuracy of the Kalman Filter state estimate $\hat{x}(t)$ immediately following meals and meal insulin boluses. In the time immediately following meals, the CGS measurement is generally more accurate than the Kalman Filter state estimate, since the model at the core of the state estimation procedure does not assume knowledge of meal timing and meal amounts. To account for this, we have developed a weighting scheme that places more weight ($w_2 \approx 1$) on the CGS measurement signal in the time following the detection of a large bolus of insulin that is typically associated with a meal.

Figure 5:
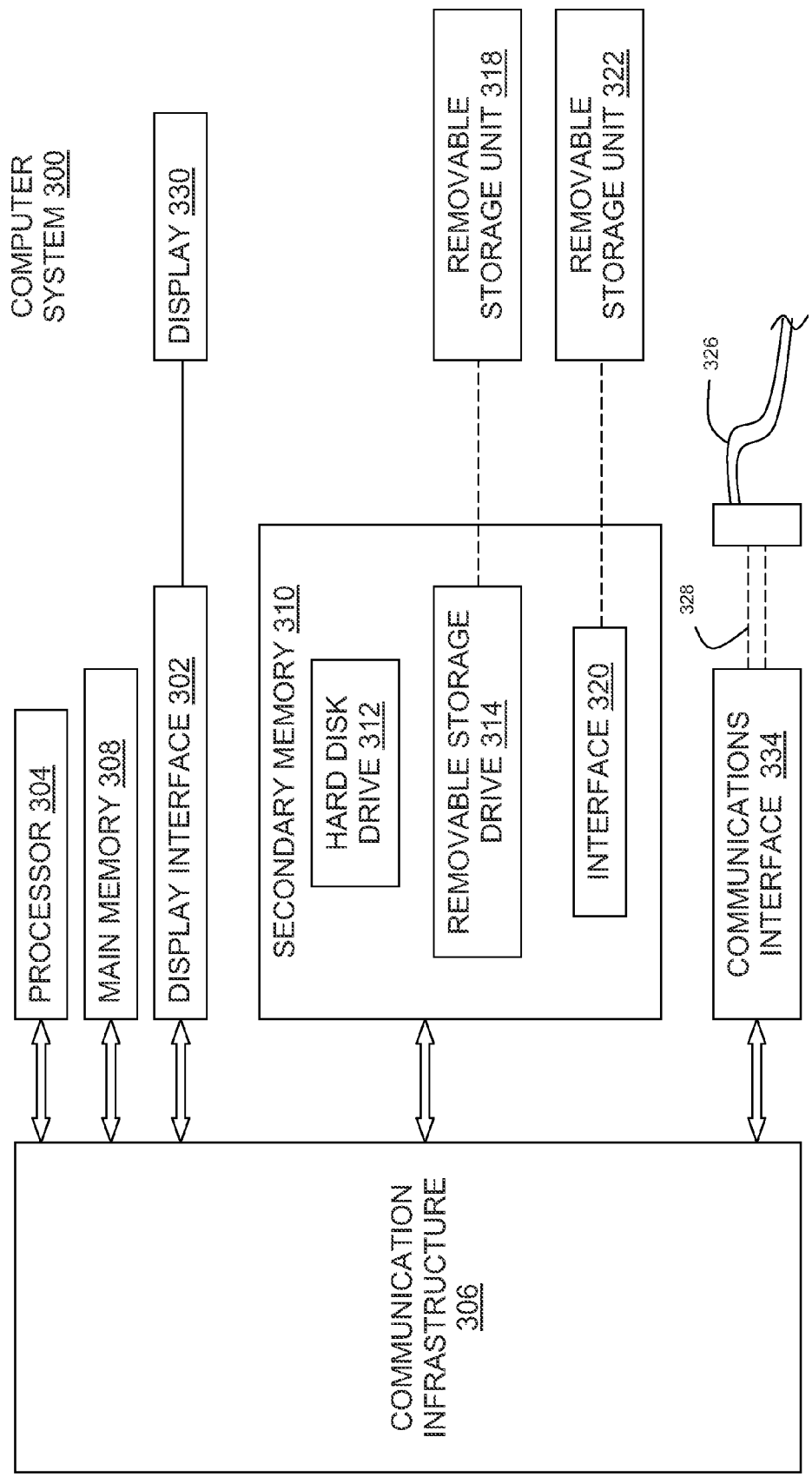
FIG. 5 is a schematic block diagram for a system or related method of an embodiment of the present invention in whole or in part.

FIG. 5 is a functional block diagram for a computer system 300 for implementation of an exemplary embodiment or portion of an embodiment of present invention. For example, a method or system of an embodiment of the present invention may be implemented using hardware, software or a combination thereof and may be implemented in one or more computer systems or other processing systems, such as personal digit assistants (PDAs) equipped with adequate memory and processing capabilities. In an example embodiment, the invention was implemented in software running on a general purpose computer 30 as illustrated in FIG. 5. The invention call also be implemented on a microcontroller or using a processor that is located in the CGS monitor, insulin pump or other insulin delivery device, or as a standalone component (or a combination of two or more of the CGS monitor, insulin pump or other insulin delivery device, or stand alone component). The computer system 300 may includes one or more processors, such as processor 304. The Processor 304 is connected to a communication infrastructure 306 (e.g., a communications bus, cross-over bar, direct connection, or network). The computer system 300 may include a display interface 302 that forwards graphics, text, and/or other data from the communication infrastructure 306 (or from a frame buffer not shown) for display on the display unit 330. Display unit 330 may be digital and/or analog.

The computer system 300 may also include a main memory 308, preferably random access memory (RAM), and may also include a secondary memory 310. The secondary memory 310 may include, for example, a hard disk drive 312 and/or a removable storage drive 314, representing a floppy disk drive, a magnetic tape drive, an optical disk drive, a flash memory, etc. The removable storage drive 314 reads from and/or writes to a removable storage unit 318 in a well known manner. Removable storage unit 318, represents a floppy disk, magnetic tape, optical disk, etc. which is read by and written to by removable storage drive 314. As will be appreciated, the removable storage unit 318 includes a computer usable storage medium having stored therein computer software and/or data.

In alternative embodiments, secondary memory 310 may include other means for allowing computer programs or other instructions to be loaded into computer system 300. Such means may include, for example, a removable storage unit 322 and an interface 320. Examples of such removable storage units/interfaces include a program cartridge and cartridge interface (such as that found in video game devices), a removable memory chip (such as a ROM, PROM, EPROM or EEPROM) and associated socket, and other removable storage units 322 and interfaces 320 which allow software and data to be transferred from the removable storage unit 322 to computer system 300.

The computer system 300 may also include a communications interface 324. Communications interface 124 allows software and data to be transferred between computer system 300 and external devices. Examples of communications interface 324 may include a modem, a network interface (such as an Ethernet card), a communications port (e.g., serial or parallel, etc.), a PCMCIA slot and card, a modem, etc. Software and data transferred via communications interface 324 are in the form of signals 328 which may be electronic, electromagnetic, optical or other signals capable of being received by communications interface 324. Signals 328 are provided to communications interface 324 via a communications path (i.e., channel) 326. Channel 326 (or any other communication means or channel disclosed herein) carries signals 328 and may be implemented using wire or cable, fiber optics, blue tooth, a phone line, a cellular phone link, an RF link, an infrared link, wireless link or connection and other communications channels.

In this document, the terms "computer program medium" and "computer usable medium" are used to generally refer to media or medium such as various software, firmware, disks, drives, removable storage drive 314, a hard disk installed in hard disk drive 312, and signals 328. These computer program products ("computer program medium" and "computer usable medium") are means for providing software to computer system 300. The computer program product may comprise a computer useable medium having computer program logic thereon. The invention includes such computer program products. The "computer program product" and "computer useable medium" may be any computer readable medium having computer logic thereon.

Computer programs (also called computer control logic or computer program logic) are may be stored in main memory 308 and/or secondary memory 310. Computer programs may also be received via communications interface 324. Such computer programs, when executed, enable computer system 300 to perform the features of the present invention as discussed herein. In particular, the computer programs, when executed, enable processor 304 to perform the functions of the present invention. Accordingly, such computer programs represent controllers of computer system 300.

In an embodiment where the invention is implemented using software, the software may be stored in a computer program product and loaded into computer system 300 using removable storage drive 314, hard drive 312 or communications interface 324. The control logic (software or computer program logic), when executed by the processor 304, causes the processor 304 to perform the functions of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language or C++ programming language, but could be implemented in other various programs, computer simulation and computer-aided design, computer simulation environment, MATLAB, or any other software platform or program, windows interface or operating system (or other operating system) or other programs known or available to those skilled in the art.

It should be appreciated that the modules and components of FIGS. 1 and 5 may be transmitted to the appropriate or desired computer networks in various locations and sites (local and/or remote) as desired or required.

The modules and components of FIGS. 1 and 5 may be transmitted to the appropriate or desired computer networks in various locations and sites (local and/or remote) via the desired or required communication links.

It should be appreciated that any of the components/modules discussed in FIGS. 1 and 5 may be integrally contained within one or more housings or separated and/or duplicated in different housings. Similarly, any of the components and modules discussed in FIGS. 1 and 5 may be duplicated more than once. Moreover, various components and modules may be adapted to replace another component or module to perform the intended function.

It should be appreciated that the modules and components as depicted in FIGS. 1 and 5 may be implemented with any location, person, staff, physician, caregiver, system, device or equipment at any healthcare provider, hospital, clinic, university, vehicle, trailer, or home, as well as any other location, premises, or organization as desired or required.

Validation of the Method

The exemplary method has been validated using in silico experiments with N=100 virtual subjects with type 1 diabetes who were equipped with virtual sensors prone to errors that are typical for CGS observed in vivo. A detailed description of the simulation environment has been presented previously [26,27]. The Table of FIG. 6 presents summary results from these experiments using the A-zone (Accurate readings) of the Continuous Glucose Error-Grid Analysis [CG-EGA, 12]. It is evident that the accuracy of the CGS is increased by the method by more than 10% within the critical hypoglycemic range, a difference that is highly statistically significant. In the euglycemic and hyperglycemic ranges, sensor accuracy is typically high [18,23] and the method provides only a marginal improvement, or equivalent accuracy results. The results are presented without weighting (i.e. $w_1=1$ regardless of BG level) and with LBGI-based weighting. The table of FIG. 6 shows the improvement in sensor accuracy when insulin delivery data is used and how each of these methods would have certain advantages, depending on the structure and the magnitude of sensor noise.

Figure 7:
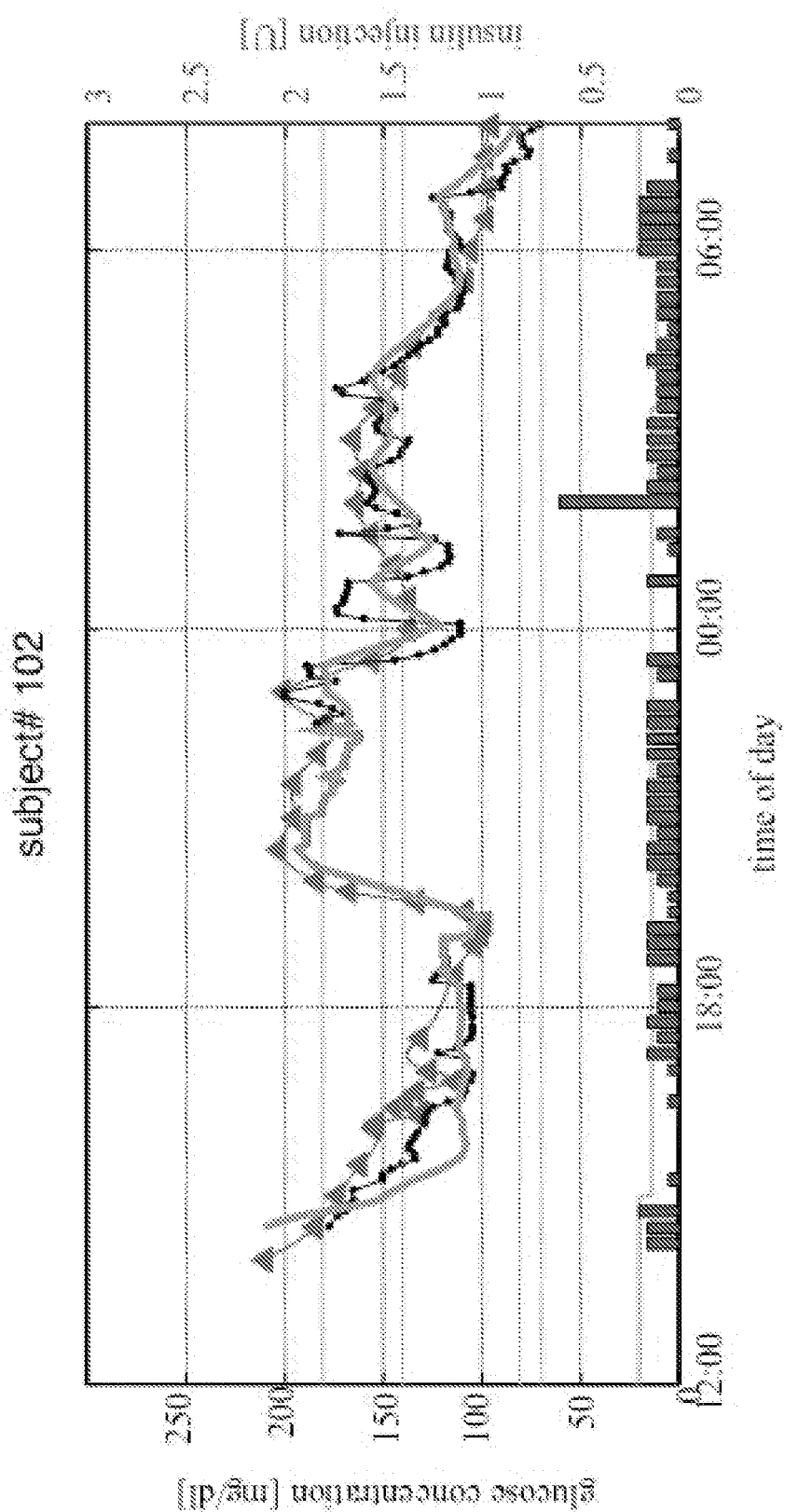
FIG. 7 graphically demonstrates the use of our weighting scheme to improve the accuracy of the CGS measurement signal using the weighting scheme, which places all weight on the CGS measurement signal following the detection of large bolus insulin amounts
Figure 9:
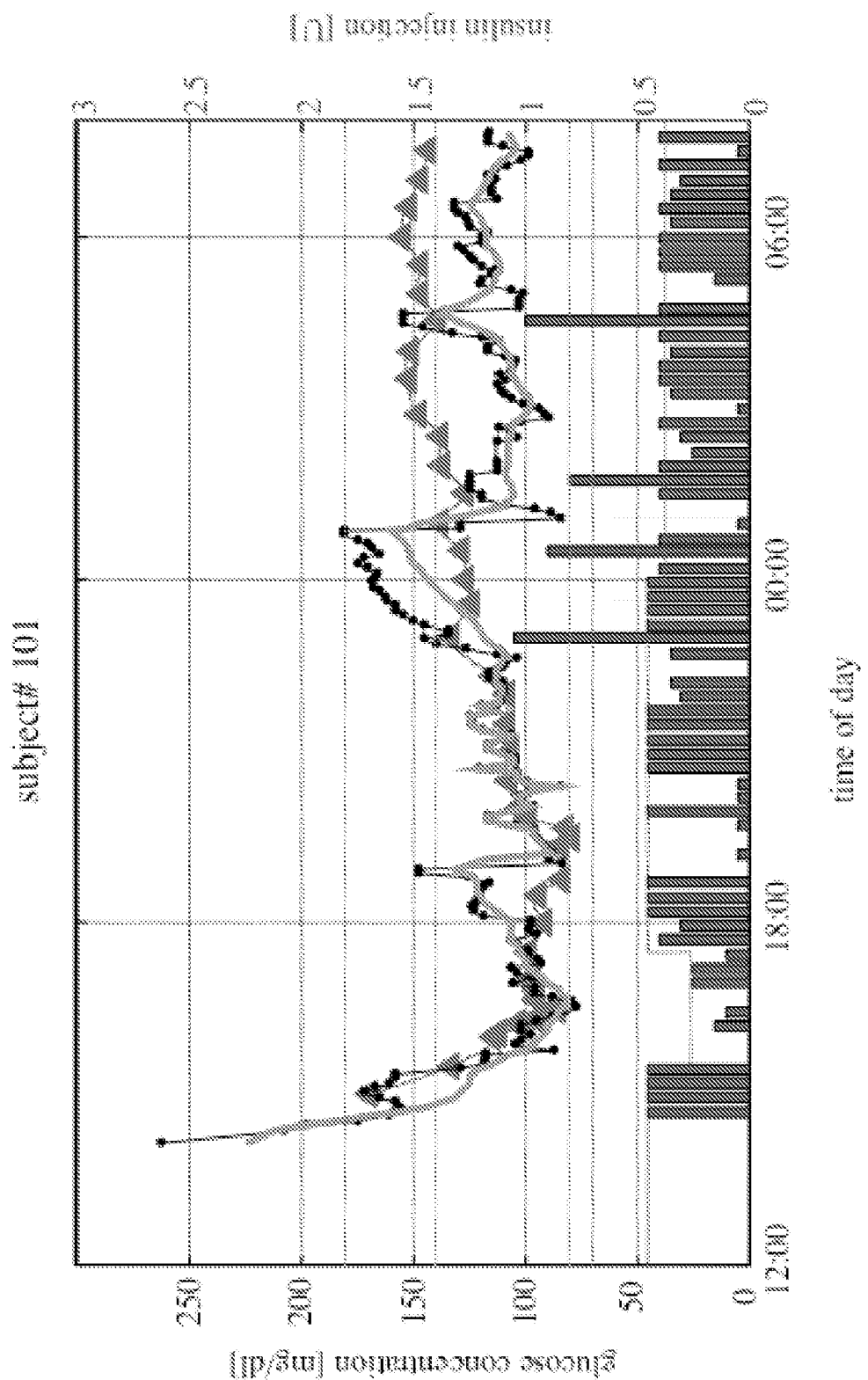
FIG. 9 graphically provides another example of the use of our weighting scheme to improve the accuracy of the CGS measurement signal using the weighting scheme which places all weight on the CGS measurement signal following the detection of large bolus insulin amounts.

The weighting scheme to improve accuracy of the CGS is further validated using real data from recent clinical trials conducted at the University of Virginia, where we have access to CGS measurement signal every 5 minutes (unless the sensor is operating in a faulty mode) and we obtain a reference blood glucose measurement every 30 minutes using a YSI glucose analyzer. FIGS. 7 & 9 graphically show traces of actual patient data from a clinical trial conducted at the University of Virginia. The trace as shown with dotted symbols is the CGS measurement signal with data obtained every 5 minutes, the trace as shown with triangle symbols tracks the reference blood glucose signal obtained every 30 minutes using a YSI glucose analyzer, and the trace as shown with the solid line represents the trace obtained using our state estimation and weighting procedure.

FIG. 7 graphically demonstrates the use of our weighting scheme to improve the accuracy of the CGS measurement signal using the weighting scheme which places all weight on the CGS measurement signal following the detection of large bolus insulin amounts. The Table of FIG. 8 describes the % A Zone of the EGA for this real patient data. FIG. 8 shows the improvement in sensor accuracy when insulin delivery data is used for real CGS measurements and insulin delivery data with regard to the trial in FIG. 7.

FIG. 9 provides another example of the use of our weighting scheme to improve the accuracy of the CGS measurement signal using the weighting scheme which places all weight on the CGS measurement signal following the detection of large bolus insulin amounts. The Table of FIG. 10 describes the % A Zone of the EGA for this real patient data. FIG. 10 shows the improvement in sensor accuracy when insulin delivery data is used for real CGS measurements and insulin delivery data with regard to the trial in FIG. 9.

EXAMPLES

Practice of an aspect of an embodiment (or embodiments) of the invention will be still more fully understood from the following examples, which are presented herein for illustration only and should not be construed as limiting the invention in any way.

Example 1 includes

Example 1 includes a method for improving the accuracy of a glucose measurement device, whereby the method may comprise: using insulin delivery information to improve the accuracy of the glucose measurement device.

Example 2 may optionally include the method of example 1, wherein the glucose measurement device is a continuous glucose device.

Example 3 may optionally include the method of example 1 (as well as subject matter of one or more of any combination of examples 1-2), further comprising:
obtaining a readout from the glucose measurement device;
obtaining the insulin delivery information from an insulin delivery device;
performing a first intermediary computation to obtain an output of the first intermediary computation using the readout from the glucose measurement device of the subject and the insulin delivery information; and performing a second intermediary computation to obtain an output of the second intermediary computation using the output of the first intermediary computation.

Example 4 may optionally include the method of example 3 (as well as subject matter of one or more of any combination of examples 1-3), wherein the glucose measurement device is a continuous glucose device.

Example 5 may optionally include the method of example 3 (as well as subject matter of one or more of any combination of examples 1-4), wherein the first intermediary computation further comprises a Kalman Filter methodology.

Example 6 may optionally include the method of example 3 (as well as subject matter of one or more of any combination of examples 1-5), wherein the first intermediary computation further comprises a method for filtering/state estimation, such as a H-infinity filtering method, a Bayesian filtering method, a Monte Carlo method, or a least squares method.

Example 7 may optionally include the method of example 3 (as well as subject matter of one or more of any combination of examples 1-6), wherein the readout from the glucose measurement device provides a frequent glucose readout.

Example 8 may optionally include the method of example 7 (as well as subject matter of one or more of any combination of examples 1-7), wherein the frequency of the readout from the glucose measurement device is at least approximately 60 minute intervals.

Example 9 may optionally include the method of example 7 (as well as subject matter of one or more of any combination of examples 1-8), wherein the frequency of the readout from the glucose measurement device is at least approximately 30 minute intervals.

Example 10 may optionally include the method of example 7 (as well as subject matter of one or more of any combination of examples 1-9), wherein the frequency of the readout from the glucose measurement device is at least approximately 15 minute intervals.

Example 11 may optionally include the method of example 3 (as well as subject matter of one or more of any combination of examples 1-10), wherein the insulin delivery information is provided by an insulin pump, artificial pancreas, or another insulin delivery device.

Example 12 may optionally include the method of example 3 (as well as subject matter of one or more of any combination of examples 1-11), wherein the insulin delivery information is provided by a measuring device.

Example 13 may optionally include the method of example 3 (as well as subject matter of one or more of any combination of examples 1-12), wherein the second intermediary computation further comprises:

inferring the output of the second intermediary computation from the output of the first intermediary computation.

Example 14 may optionally include the method of example 13 (as well as subject matter of one or more of any combination of examples 1-13), wherein inferring the second intermediary computation further comprises:

extrapolating the output of the first intermediary computation to some future time to determine an extrapolated state vector output.

Example 15 may optionally include the method of example 14 (as well as subject matter of one or more of any combination of examples 1-14), wherein determining the extrapolated output is provided by $$\hat{x}(t|t-\tau) = A^\tau \hat{x}(t-\tau) + A(\tau)Bu(t-\tau) + A(\tau)G\omega(t-\tau),$$

wherein $\hat{x}(t|t-\tau)$ refers to the extrapolated state vector output;

A is a state space matrix;

B is a state space matrix;

G is a state space matrix;

$A^\tau = A \cdot A \ldots A$, i.e. the $\tau$-fold composition of the state space matrix A;

$A(\tau) = \Sigma_{s=0}^{\tau-1} A^s$, with $A(0) = 0_{8 \times 8}$.

Example 16 may optionally include the method of example 15 (as well as subject matter of one or more of any combination of examples 1-15), wherein the state space matrix A is:

$$A = \begin{bmatrix} .9913 & -102.7 & -1.50 \times 10^{-8} & -2.89 \times 10^{-6} & -4.1 \times 10^{-4} & 0 & 2.01 \times 10^{-6} & 4.3 \times 10^{-5} \\ 0 & .839 & 5.23 \times 10^{-10} & 7.44 \times 10^{-8} & 6.84 \times 10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9 \times 10^{-4} & .0180 & .7882 & 0 & 0 & 0 \\ .0865 & -4.667 & -2.73 \times 10^{-10} & -6.59 \times 10^{-8} & -1.26 \times 10^{-5} & .9131 & 6.00 \times 10^{-8} & 1.90 \times 10^{-6} \\ 0 & 0 & 0 & 0 & 0 & 0 & .9083 & 0 \\ 0 & 0 & 0 & 0 & 0 & 0 & .09115 & .9891 \end{bmatrix}.$$

Example 17 may optionally include the method of example 15 (as well as subject matter of one or more of any combination of examples 1-16), wherein the state space matrix B is:

$$B^T = [-3.05 \times 10^{-9}\ 1.34 \times 10^{-10}\ 0.9900\ 0.0100\ 6.50 \times 10^{-5}\ -4.61 \times 10^{-11}\ 0\ 0].$$

Example 18 may optionally include the method of example 15 (as well as subject matter of one or more of any combination of examples 1-17), wherein the state space matrix G is:

$$G^T = [6.76 \times 10^{-7}\ 0\ 0\ 0\ 0\ 1.52 \times 10^{-8}\ 0.9534\ 0.0464].$$

Example 19 may optionally include the method of example 14 (as well as subject matter of one or more of any combination of examples 1-18), wherein the second intermediary computation further comprises:

extracting a blood glucose state from the extrapolated state vector output.

Example 20 may optionally include the method of example 19 (as well as subject matter of one or more of any combination of examples 1-19), wherein extracting the blood glucose state from the extrapolated value further comprises:

applying a state space matrix to the extrapolated state vector output.

Example 21 may optionally include the method of example 3 (as well as subject matter of one or more of any combination of examples 1-20), further comprising:

performing a third computation to reach an estimate of the blood glucose of the subject by applying a weighting scheme to the readout from the glucose measurement device and the output of the second intermediary computation.

Example 22 may optionally include the method of example 21 (as well as subject matter of one or more of any combination of examples 1-21), wherein the weighting scheme further comprises:

applying a first weighting coefficient to the readout from the glucose measurement device and applying a second weighting coefficient to the output of the second intermediary computation.

Example 23 may optionally include the method of example 22 (as well as subject matter of one or more of any combination of examples 1-22), wherein the weighting yields a linear combination of the readout from the glucose measurement device and the output of the second intermediary so that the sum of the first weighting coefficient and the second weighting coefficient is equal to 1.

Example 24 may optionally include the method of example 22 (as well as subject matter of one or more of any combination of examples 1-23), wherein the weighting scheme further comprises:

applying more weight to the output of the second intermediary computation during hypoglycemia.

Example 25 may optionally include the method of example 24 (as well as subject matter of one or more of any combination of examples 1-24), wherein the more weight is approximately 1.

Example 26. may optionally include the method of example 22 (as well as subject matter of one or more of any combination of examples 1-25), wherein the weighting scheme further comprises:

applying more weight to the readout from the glucose measurement device during euglycemia.

Example 27 may optionally include the method of example 26 (as well as subject matter of one or more of any combination of examples 1-26), wherein the more weight is approximately 1.

Example 28 may optionally include the method of example 22 (as well as subject matter of one or more of any combination of examples 1-27), wherein the weighting scheme further comprises:

applying more weight to the readout from the glucose measurement device during hyperglycemia.

Example 29 may optionally include the method of example 28 (as well as subject matter of one or more of any combination of examples 1-28), wherein the more weight is approximately 1.

Example 30 may optionally include the method of example 22 (as well as subject matter of one or more of any combination of examples 1-29), wherein the weighting scheme further comprises:

applying a weighting scheme that accounted for the lack of accuracy of the output of the second intermediary computation immediately following meals and meal insulin boluses.

Example 31 may optionally include the method of example 22 (as well as subject matter of one or more of any combination of examples 1-30), wherein the weighting scheme further comprises:

applying more weight on the readout from the glucose measurement device in the time following a detection of a large bolus of insulin.

Example 32 may optionally include the method of example 22 (as well as subject matter of one or more of any combination of examples 1-31), wherein the weighting scheme further comprises:

basing the weighting scheme on an S-shaped curve with the curve increasing at approximately the threshold of hypoglycemia.

Example 33 may optionally include the method of example 22 (as well as subject matter of one or more of any combination of examples 1-32), wherein the first weighting coefficient and the second weighting coefficient are provided by the formula $w_1 = LBGI(CGS-50)/100$ where LBGI is a low BG index and CGS is the readout from the continuous glucose measurement device.

Example 34 includes a system for improving the accuracy of a glucose measurement device, wherein the glucose measurement device may uses insulin delivery information (among other data and information) to improve the accuracy of the glucose measurement device.

Example 35 may optionally include the system of example 34 (as well as subject matter of one or more of any combination of examples 1-34), wherein the glucose measurement device is a continuous glucose device.

Example 36 may optionally include the system of example 34 (as well as subject matter of one or more of any combination of examples 1-35), further comprising:

the glucose measurement device configured to provide a readout;

an insulin delivery device configured to provide the insulin delivery information; and a processor, wherein the processor is configured to provide:
a first intermediary computation that provides an output of the first intermediary computation using the readout from the glucose measurement device of the subject and the insulin delivery information, and
a second intermediary computation that provides an output of the second intermediary computation using the output of the first intermediary computation.

Example 37 may optionally include the system of example 36 (as well as subject matter of one or more of any combination of examples 1-36), wherein the glucose measurement device is a continuous glucose device.

Example 38 may optionally include the system of example 36 (as well as subject matter of one or more of any combination of examples 1-37), wherein the first intermediary computation further comprises a Kalman Filter methodology.

Example 39 may optionally include the system of example 36 (as well as subject matter of one or more of any combination of examples 1-38), wherein the first intermediary computation further comprises a method for filtering/state estimation, such as a H-infinity filtering method, a Bayesian filtering method, a Monte Carlo method, or a least squares method.

Example 40 may optionally include the system of example 36 (as well as subject matter of one or more of any combination of examples 1-39), wherein the readout from the glucose measurement device provides a frequent glucose readout.

Example 41 may optionally include the system of example 40 (as well as subject matter of one or more of any combination of examples 1-40), wherein the frequency of the readout from the glucose measurement device is at least approximately 60 minute intervals.

Example 42 may optionally include the system of example 40 (as well as subject matter of one or more of any combination of examples 1-41), wherein the frequency of the readout from the glucose measurement device is at least approximately 30 minute intervals.

Example 43 may optionally include the system of example 40 (as well as subject matter of one or more of any combination of examples 1-42), wherein the frequency of the readout from the glucose measurement device is at least approximately 15 minute intervals.

Example 44 may optionally include the system of example 36 (as well as subject matter of one or more of any combination of examples 1-43), wherein the insulin delivery information is provided by an insulin pump, artificial pancreas, or another insulin delivery device.

Example 45 may optionally include the system of example 36 (as well as subject matter of one or more of any combination of examples 1-44), wherein the insulin delivery information is provided by a measuring device.

Example 46 may optionally include the system of example 36 (as well as subject matter of one or more of any combination of examples 1-45), wherein the second intermediary computation further comprises:
an inference of the output of the second intermediary computation from the output of the first intermediary computation.

Example 47 may optionally include the system of example 46 (as well as subject matter of one or more of any combination of examples 1-46), wherein inferring the second intermediary computation further comprises:
an extrapolation of the output of the first intermediary computation to some future time to determine an extrapolated state vector output.

Example 48 may optionally include the system of example 47 (as well as subject matter of one or more of any combination of examples 1-47), wherein the extrapolated output is determined by $$\hat{x}(t|t-\tau) = A^\tau \hat{x}(t-\tau) + A(\tau)Bu(t-\tau) + A(\tau)G\omega(t-\tau),$$

wherein
$\hat{x}(t|t-\tau)$ refers to the extrapolated state vector output;
A is a state space matrix;
B is a state space matrix;
G is a state space matrix;
$A^\tau = A \cdot A \ldots A$, i.e. the $\tau$-fold composition of the state space matrix A;
$A(\tau) = \Sigma_{s=0}^{\tau-1} A^s$, with $A(0) = 0_{8\times8}$.

Example 49 may optionally include the system of example 48 (as well as subject matter of one or more of any combination of examples 1-48), wherein the state space matrix A is:

$$A = \begin{vmatrix} .9913 & -102.7 & -1.50\times10^{-8} & -2.89\times10^{-6} & -4.1\times10^{-4} & 0 & 2.01\times10^{-6} & 4.30\times10^{-5} \\ 0 & .839 & 5.23\times10^{-10} & 7.44\times10^{-8} & 6.84\times10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9\times10^{-4} & .0180 & .7882 & 0 & 0 & 0 \\ .0865 & -4.667 & -2.73\times10^{-10} & -6.59\times10^{-8} & -1.26\times10^{-5} & .9131 & 6.00\times10^{-8} & 1.90\times10^{-6} \\ 0 & 0 & 0 & 0 & 0 & 0 & .9083 & 0 \\ 0 & 0 & 0 & 0 & 0 & 0 & .09115 & .9891 \end{vmatrix}.$$

Example 50 may optionally include the system of example 48 (as well as subject matter of one or more of any combination of examples 1-49), wherein the state space matrix B is:

$$B^T = [-3.05\times10^{-9}\ 1.34\times10^{-10}\ 0.9900\ 0.0100\ 6.50\times10^{-5}\ -4.61\times10^{-11}\ 0\ 0].$$

Example 51. The system of example 48, (as well as subject matter of one or more of any combination of examples 1-50), wherein the state space matrix G is:

$$G^T = [6.76\times10^{-7}\ 0\ 0\ 0\ 0\ 1.52\times10^{-8}\ 0.9534\ 0.0464].$$

Example 52 may optionally include the system of example 47 (as well as subject matter of one or more of any combination of examples 1-51), wherein the second intermediary computation further comprises:
an extraction of a blood glucose state from the extrapolated state vector output.

Example 53 may optionally include the system of example 52 (as well as subject matter of one or more of any combination of examples 1-52), wherein the extraction of the blood glucose state from the extrapolated value further comprises:
an application of a state space matrix to the extrapolated state vector output.

Example 54 may optionally include the system of example 36 (as well as subject matter of one or more of any combination of examples 1-53), wherein the processor is configured to provide a third computation to reach an estimate of the blood glucose of the subject by applying a weighting scheme to the readout from the glucose measurement device and the output of the second intermediary computation.

Example 55 may optionally include the system of example 54 (as well as subject matter of one or more of any combination of examples 1-54), wherein the weighting scheme further comprises:
an application of a first weighting coefficient to the readout from the glucose measurement device and applying a second weighting coefficient to the output of the second intermediary computation.

Example 56 may optionally include the system of example 55 (as well as subject matter of one or more of any combination of examples 1-55), wherein the weighting yields a linear combination of the readout from the glucose measurement device and the output of the second intermediary so that the sum of the first weighting coefficient and the second weighting coefficient is equal to 1.

Example 57 may optionally include the system of example 55 (as well as subject matter of one or more of any combination of examples 1-56), wherein the weighting scheme further comprises:
an application of more weight to the output of the second intermediary computation during hypoglycemia.

Example 58 may optionally include the system of example 57 (as well as subject matter of one or more of any combination of examples 1-57), wherein the more weight is approximately 1.

Example 59 may optionally include the system of example 55 (as well as subject matter of one or more of any combination of examples 1-58), wherein the weighting scheme further comprises:
an application of more weight to the readout from the glucose measurement device during euglycemia.

Example 60 may optionally include the system of example 59 (as well as subject matter of one or more of any combination of examples 1-59), wherein the more weight is approximately 1.

Example 61 may optionally include the system of example 55 (as well as subject matter of one or more of any combination of examples 1-60), wherein the weighting scheme further comprises:

an application of more weight to the readout from the glucose measurement device during hyperglycemia.

Example 62 may optionally include the system of example 61 (as well as subject matter of one or more of any combination of examples 1-61), wherein the more weight is approximately 1.

Example 63 may optionally include the system of example 55 (as well as subject matter of one or more of any combination of examples 1-62), wherein the weighting scheme further comprises:

an application of a weighting scheme that accounted for the lack of accuracy of the output of the second intermediary computation immediately following meals and meal insulin boluses.

Example 64 may optionally include the system of example 55 (as well as subject matter of one or more of any combination of examples 1-63), wherein the weighting scheme further comprises:

an application of more weight on the readout from the glucose measurement device in the time following a detection of a large bolus of insulin.

Example 65 may optionally include the system of example 55 (as well as subject matter of one or more of any combination of examples 1-64), wherein the weighting scheme further comprises:

an application of the weighting scheme based on an S-shaped curve with the curve increasing at approximately the threshold of hypoglycemia.

Example 66 may optionally include the system of example 55 (as well as subject matter of one or more of any combination of examples 1-65), wherein the first weighting coefficient and the second weighting coefficient are provided by the formula $w_1=LBGI(CGS-50)/100$ where LBGI is a low BG index and CGS is the readout from the continuous glucose measurement device.

Example 67 includes a computer program product comprising a computer useable medium having a computer program logic for enabling at least one processor in a computer system for improving the accuracy of a glucose measurement device. The computer program logic may comprise: using insulin delivery information (as well as other possible information or data) to improve the accuracy of the glucose measurement device.

Example 68 may optionally include the computer program product of example 67 (as well as subject matter of one or more of any combination of examples 1-67), wherein the glucose measurement device is a continuous glucose device.

Example 69 may optionally include the computer program product of example 67 (as well as subject matter of one or more of any combination of examples 1-68), wherein the computer logic further comprises:

obtaining a readout from the glucose measurement device;
obtaining the insulin delivery information from an insulin delivery device;
performing a first intermediary computation to obtain an output of the first intermediary computation using the readout from the glucose measurement device of the subject and the insulin delivery information; and
performing a second intermediary computation to obtain an output of the second intermediary computation using the output of the first intermediary computation.

Example 70 may optionally include the computer program product of example 69 (as well as subject matter of one or more of any combination of examples 1-69), wherein the glucose measurement device is a continuous glucose device.

Example 71 may optionally include the computer program product of example 69 (as well as subject matter of one or more of any combination of examples 1-70), wherein the first intermediary computation further comprises a Kalman Filter methodology.

Example 72 may optionally include the computer program product of example 69 (as well as subject matter of one or more of any combination of examples 1-71), wherein the first intermediary computation further comprises a method for filtering/state estimation, such as a H-infinity filtering method, a Bayesian filtering method, a Monte Carlo method, or a least squares method.

Example 73 may optionally include the computer program product of example 69 (as well as subject matter of one or more of any combination of examples 1-72), wherein the readout from the glucose measurement device provides a frequent glucose readout.

Example 74 may optionally include the computer program product of example 73 (as well as subject matter of one or more of any combination of examples 1-73), wherein the frequency of the readout from the glucose measurement device is at least approximately 60 minute intervals.

Example 75 may optionally include the computer program product of example 73 w(as well as subject matter of one or more of any combination of examples 1-74), herein the frequency of the readout from the glucose measurement device is at least approximately 30 minute intervals.

Example 76 may optionally include the computer program product of example 73 (as well as subject matter of one or more of any combination of examples 1-75), wherein the frequency of the readout from the glucose measurement device is at least approximately 15 minute intervals.

Example 77 may optionally include the computer program product of example 69 (as well as subject matter of one or more of any combination of examples 1-76), wherein the insulin delivery information is provided by an insulin pump, artificial pancreas, or another insulin delivery device.

Example 78 may optionally include the computer program product of example 69 (as well as subject matter of one or more of any combination of examples 1-77), wherein the insulin delivery information is provided by a measuring device.

Example 79 may optionally include the computer program product of example 69 (as well as subject matter of one or more of any combination of examples 1-78), wherein the second intermediary computation further comprises:

inferring the output of the second intermediary computation from the output of the first intermediary computation.

Example 80 may optionally include the computer program product of example 79 (as well as subject matter of one or more of any combination of examples 1-79), wherein inferring the second intermediary computation further comprises:

extrapolating the output of the first intermediary computation to some future time to determine an extrapolated state vector output.

Example 81 may optionally include the computer program product of example 80 (as well as subject matter of one or more of any combination of examples 1-80), wherein determining the extrapolated output is provided by $$\hat{x}(t|t-\tau)=A^\tau \hat{x}(t-\tau)+A(\tau)Bu(t-\tau)+A(\tau)G\omega(t-\tau),$$

wherein
$\hat{x}(t|t-\tau r)$ refers to the extrapolated state vector output;
A is a state space matrix;
B is a state space matrix;
G is a state space matrix;

$A^\tau = A \cdot A \ldots A$, i.e. the $\tau$-fold composition of the state space matrix A;

$A(\tau) = \Sigma_{s=0}^{\tau-1} A^s$, with $A(0) = 0_{8 \times 8}$.

Example 82. The computer program product of example 81 (as well as subject matter of one or more of any combination of examples 1-81), wherein the state space matrix A is:

$$A = \begin{bmatrix} .9913 & -102.7 & -1.50 \times 10^{-8} & -2.89 \times 10^{-6} & -4.1 \times 10^{-4} & 0 & 2.01 \times 10^{-6} & 4.30 \times 10^{-5} \\ 0 & .839 & 5.23 \times 10^{-10} & 7.44 \times 10^{-8} & 6.84 \times 10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9 \times 10^{-4} & .0180 & .7882 & 0 & 0 & 0 \\ .0865 & -4.667 & -2.73 \times 10^{-10} & -6.59 \times 10^{-8} & -1.26 \times 10^{-5} & .9131 & 6.00 \times 10^{-8} & 1.90 \times 10^{-6} \\ 0 & 0 & 0 & 0 & 0 & 0 & .9083 & 0 \\ 0 & 0 & 0 & 0 & 0 & 0 & .09115 & .9891 \end{bmatrix}.$$

Example 83 may optionally include the computer program product of example 81 (as well as subject matter of one or more of any combination of examples 1-82), wherein the state space matrix B is:

$B^T = [-3.05 \times 10^{-9}\ 1.34 \times 10^{-10}\ 0.9900\ 0.0100\ 6.50 \times 10^{-5}\ -4.61 \times 10^{-11}\ 0\ 0]$.

Example 84 may optionally include the computer program product of example 81 (as well as subject matter of one or more of any combination of examples 1-83), wherein the state space matrix G is:

$G^T = [6.76 \times 10^{-7}\ 0\ 0\ 0\ 0\ 1.52 \times 10^{-8}\ 0.9534\ 0.0464]$

Example 85 may optionally include the computer program product of example 80 (as well as subject matter of one or more of any combination of examples 1-84), wherein the second intermediary computation further comprises:

extracting a blood glucose state from the extrapolated state vector output.

Example 86 may optionally include the computer program product of example 85 (as well as subject matter of one or more of any combination of examples 1-85), wherein extracting the blood glucose state from the extrapolated value further comprises:

applying a state space matrix to the extrapolated state vector output.

Example 87 may optionally include the computer program product of example 69 (as well as subject matter of one or more of any combination of examples 1-86), further comprising:

performing a third computation to reach an estimate of the blood glucose of the subject by applying a weighting scheme to the readout from the glucose measurement device and the output of the second intermediary computation.

Example 88 may optionally include the computer program product of example 87 (as well as subject matter of one or more of any combination of examples 1-87), wherein the weighting scheme further comprises:

applying a first weighting coefficient to the readout from the glucose measurement device and applying a second weighting coefficient to the output of the second intermediary computation.

Example 89 may optionally include the computer program product of example 88 (as well as subject matter of one or more of any combination of examples 1-88), wherein the weighting yields a linear combination of the readout from the glucose measurement device and the output of the second intermediary so that the sum of the first weighting coefficient and the second weighting coefficient is equal to 1.

Example 90 may optionally include the computer program product of example 88 (as well as subject matter of one or more of any combination of examples 1-89), wherein the weighting scheme further comprises:

applying more weight to the output of the second intermediary computation during hypoglycemia.

Example 91 may optionally include the computer program product of example 90 wherein(as well as subject matter of one or more of any combination of examples 1-90), the more weight is approximately 1.

Example 92 may optionally include the computer program product of example 88 (as well as subject matter of one or more of any combination of examples 1-91), wherein the weighting scheme further comprises:

applying more weight to the readout from the glucose measurement device during euglycemia.

Example 93 may optionally include the computer program product of example 92 (as well as subject matter of one or more of any combination of examples 1-92), wherein the more weight is approximately 1.

Example 94 may optionally include the computer program product of example 88 (as well as subject matter of one or more of any combination of examples 1-93), wherein the weighting scheme further comprises:

applying more weight to the readout from the glucose measurement device during hyperglycemia.

Example 95 may optionally include the computer program product of example 94 (as well as subject matter of one or more of any combination of examples 1-94), wherein the more weight is approximately 1.

Example 96 may optionally include the computer program product of example 88 (as well as subject matter of one or more of any combination of examples 1-95), wherein the weighting scheme further comprises:

applying a weighting scheme that accounted for the lack of accuracy of the output of the second intermediary computation immediately following meals and meal insulin boluses.

Example 97 may optionally include the computer program product of example 88 (as well as subject matter of one or more of any combination of examples 1-96), wherein the weighting scheme further comprises:

applying more weight on the readout from the glucose measurement device in the time following a detection of a large bolus of insulin.

Example 98 may optionally include the computer program product of example 88 (as well as subject matter of one or more of any combination of examples 1-97), wherein the weighting scheme further comprises:

basing the weighting scheme on an S-shaped curve with the curve increasing at approximately the threshold of hypoglycemia.

Example 99 may optionally include the computer program product of example 88 (as well as subject matter of one or more of any combination of examples 1-98), wherein the first weighting coefficient and the second weighting coefficient are provided by the formula $w_1=LBGI(CGS-50)/100$ where LBGI is a low BG index and CGS is the readout from the continuous glucose measurement device.

Example 100 can include, or can optionally be combined with any portion or combination of any portions of any one or more of Examples 1-99 to include, subject matter that can include means for performing any one or more of the functions of Examples 1-99, or a machine-readable medium including instructions that, when performed by a machine, cause the machine to perform any one or more of the functions of Examples 1-99.

Example 101 can include, or can optionally be combined with any portion or combination of any portions of any one or more of Examples 1-99 to include, subject matter that can include means for performing any one or more of the functions of Examples 1-99, as well devices, systems, structures, components, compositions, materials, shapes, contours, and sizes. Moreover, any of the means discussed throughout examples 1-99 may optionally be performed by any structure, component, device or system discussed throughout this disclosure or any disclosure incorporated by reference herein.

Example 102 can include, or can optionally be combined with any portion or combination of any portions of any one or more of Examples 1-99 to include, subject matter that can include means for manufacturing any one or more of the components, systems, devices, elements, compositions, material, and/or computer program product of Examples 1-99. The subject matter and means may also be provided from the disclosure provided herein, as well as any references incorporated herein by reference.

REFERENCES

The following patents, applications and publications as listed below and throughout this document are hereby incorporated by reference in their entirety herein.

The devices, systems, computer program products, components, and methods of various embodiments of the invention disclosed herein may utilize aspects disclosed in the following references, applications, publications and patents and which are hereby incorporated by reference herein in their entirety:

1. Klonoff, D: Continuous Glucose Monitoring: Roadmap for the 21$^{st}$ Century Diabetes Therapy. Diabetes Care 288: 1231-1239, 2005.
2. Garg, K, Zisser, H, Schwartz, S, Bailey, T, Kaplan, R, Ellis, S, Jovanovic, L:Improvement in Glycemic Excursions With a Transcutaneous, Real-time Continuous Glucose Sensor. Diabetes Care 29:44-50, 2006.
3. Deiss, D, Bolinder, J, Riveline, J, Battelino, T, Bosi, E, Tubiana-Rufi, N, Kerr, D, Phillip, M: Improved Glycemic Control in Poorly Controlled Patients with Type 1 Diabetes Using Real-Time Continuous Glucose Monitoring. Diabetes Care 29: 2730-2732, 2006.
4. Kovatchev, B, Clarke, W: Continuous Glucose Monitoring (CGM)) reduces risks for hypo- and hyperglycemia and glucose variability in T1DM and insulin-treated T2DM, Diabetes 56 (Suppl 1): A23, 2007.
5. Steil, G, Rebrin, K, Darwin, C, Hariri, F, Saad, M: Feasibility of Automating Insulin Delivery for the Treatment of Type 1 Diabetes. Diabetes 55:3344-3355, 2006.
6. Hovorka, R: Continuous glucose monitoring and closed-loop systems. Diabetic Medicine 23:1-12, 2006.
7. Renard, E: Implantable Closed-Loop Glucose-Sensing and Insulin Delivery: The Future for Insulin Pump Therapy. Curr Opin Pharmacol 2:708-716, 2002.
8. The Diabetes Research in Children Network (DirecNet) Study Group: The Accuracy of the GlucoWatch® G2™ Biographer in Children with Type 1 Diabetes: Results of the Diabetes Research in Children Network (DirecNet) Accuracy Study. Diabetes Technology & Therapeutics 5:791-800, 2003.
9. The Diabetes Research in Children Network (DirecNet) Study Group: The Accuracy of the CGMS™ in Children with Type 1 Diabetes: Results of the Diabetes Research in Children Network (DirecNet) Accuracy Study. Diabetes Technology & Therapeutics 5: 781-789, 2003.
10. Wenholt, I, Vollebregt, M, Hart, A, Hoekstra, J, Devries, J: Comparison of a Needle-type and a Microdialysis Continuous Glucose Monitor in Type 1 Diabetic Patients. Diabetes Care 28:2871-2876, 2005.
11. Wilson, D Beck, R, Tamborlane, W, Dontchev; M, Kollman, C, Chase, P, Fox, L, Ruedy, K Tsalikian, E, Weinzimer, S: The DirecNet Study Group:The Accuracy of the FreeStyle Navigator Continuous Glucose Monitoring System in Children With Type 1 Diabetes. Diabetes Care 30:1, 59-64, 2007.
12. Kovatchev, B, Gonder-Frederick, A, Cox, D, Clarke, W: Evaluating the Accuracy of Continuous Glucose-Monitoring Sensors. Diabetes Care 27:1922-1928, 2004.
13. Clarke, W, Anderson, S, Farhy, L, Breton, M, Gonder-Frederick, L, Cox, D, Kovatchev, B: Evaluating the Clinical Accuracy of Two Continuous Glucose Sensors Using Continuous Glucose-Error Grid Analysis. Diabetes Care 28:22412-2417, 2005.
14. Weinstein, R, Schwartz, S, Brazg, R, Bugler, J, Peyser, T, McGarraugh, G: Accuracy of the 5-day FreeStyle Navigator Continuous Glucose Monitoring System: comparison with frequent laboratory reference measurements. Diabetes Care 30:1125-1130, 2007.
15. US Food and Drug Administration: Review Criteria Assessment of Portable Blood Glucose Monitoring In Vitro Diagnostic Devices using Glucose Oxidase, Dehydrogenase or Hexokinase Methodology—(Version Feb. 14, 1996) www.fda.gov.
16. Clarke, W, Cox, D, Gonder-Frederick, L, Kovatchev, B: Understanding the Continuous Error-Grid Analysis—CG-EGA. Diabetes Care 30: 449-450, 2007.
17. Clarke, W L, Kovatchev, B, Continuous Glucose Sensors: Continuing Questions about Clinical Accuracy, Journal of Diabetes Science and Technology: 2007: 1:669-675.
18. Kovatchev, B, Anderson, S, Heinemann, L, Clarke, W, Comparison of the Numerical and Clinical Accuracy of Four Continuous Glucose Monitors, Diabetes Care: 2008: 31: 1160-1164.
19. Kovatchev, B, Clarke, W, Peculiarities of the Continuous Glucose Monitoring Data Stream and Their Impact on Developing Closed-Loop Control Technology, Journal of Diabetes Science and Technology: 2008: 2: 1-6.
20. Keenan D B, Mastrototaro J J, Voskanyan G, Steil G M. Delays in Minimally Invasive Continuous Glucose Monitoring Devices: A Review of Current Technology. J Diabetes Sci Technol, 3: 1207-1214, 2009.
21. King, et al., (including BP Kovatchev). Method for Improvising Accuracy of Continuous Glucose Sensors and a Continuous Glucose Sensor Using the Same, International Patent Application Serial No. PCT/US2006/033724, filed Aug. 29, 2006.

22. Breton, et al. (including BP Kovatchev), Method, system and computer program product for real-time detection of sensitivity decline in analyte sensors, International Patent Application Serial No. PCT/US2007/082744, filed Oct. 26, 2007.
23. Keenan D B, Cartaya R, Mastrototaro J J. Accuracy of a New Real-Time Continuous Glucose Monitoring Algorithm. J Diabetes Sci Technol, 4: 111-118, 2010.
24. Kovatchev B P, Breton M D. The Accuracy of a New Real-Time Continuous Glucose Monitoring Algorithm: An Analysis. J Diabetes Sci Technol, 4: 119-122, 2010.
25. Facchinetti A, Sparacino G, Cobelli C. Modeling the Error of Continuous Glucose Monitoring Sensor Data: Critical Aspects Discussed through Simulation Studies. J Diabetes Sci Technol, 4: 4-14, 2010.
26. Kovatchev B P, Breton M D, Dalla Man C, and Cobelli C. Method, System and Computer Simulation Environment for Testing of Monitoring and Control Strategies in Diabetes. PCT/US2008/067725, filed Jun. 20, 2008.
27. Kovatchev B P, Breton M D, Dalla Man C, Cobelli C (2009). In Silico Preclinical Trials: A Proof of Concept in Closed-Loop Control of Type 1 Diabetes. *J Diabetes Sci Technol* 3: 44-55.
28. Kovatchev B P, Cox D J, Gonder-Frederick L A Young-Hyman D, Schlundt D and W L Clarke (1998). Assessment of Risk for Severe Hypoglycemia Among Adults with IDDM: Validation of the Low Blood Glucose Index, Diabetes Care, 21: 1870-1875.

The devices, systems, computer program products, components, and methods of various embodiments of the invention disclosed herein may utilize aspects disclosed in the following references, applications, publications and patents and which are hereby incorporated by reference herein in their entirety:

A. International Patent Application Serial No. PCT/US2011/028163, Breton, et al., entitled "Method and System for the Safety, Analysis and Supervision of Insulin Pump Action and Other Modes of Insulin Delivery in Diabetes", filed Mar. 11, 2011.
B. International Patent Application Serial No. PCT/US2010/047711, Kovatchev, et al., "Tracking the Probability for Imminent Hypoglycemia in Diabetes from Self-Monitoring Blood Glucose (SMBG) Data", filed Sep. 2, 2010.
C. International Patent Application Serial No. PCT/US2010/047386, Kovatchev, et al., "System, Method and Computer Program Product for Adjustment of Insulin Delivery (AID) in Diabetes Using Nominal Open-Loop Profiles", filed Aug. 31, 2010.
D. International Patent Application Serial No. PCT/US2010/040097, Kovatchev, et al., "System, Method, and Computer Simulation Environment for In Silico Trials in Prediabetes and Type 2 Diabetes", filed Jun. 25, 2010.
E. International Patent Application Serial No. PCT/US2010/036629, Kovatchev, et al., "System Coordinator and Modular Architecture for Open-Loop and Closed-Loop Control of Diabetes", filed May 28, 2010 (Publication No. WO 2010/138848, Dec. 2, 2010).
F. International Patent Application Serial No. PCT/US2010/025405, Kovatchev, et al., entitled "Method, System and Computer Program Product for CGM-Based Prevention of Hypoglycemia via Hypoglycemia Risk Assessment and Smooth Reduction Insulin Delivery," filed Feb. 25, 2010.
G. International Patent Application Serial No. PCT/US2009/065725, Kovatchev, et al., filed Nov. 24, 2009, entitled "Method, System, and Computer Program Product for Tracking of Blood Glucose Variability in Diabetes from Data."
H. International Patent Application Serial No. PCT/US2008/082063, Magni, et al., entitled "Model Predictive Control Based Method for Closed-Loop Control of Insulin Delivery in Diabetes Using Continuous Glucose Sensing", filed Oct. 31, 2008; U.S. patent application Ser. No. 12/740,275, Magni, et al., entitled "Predictive Control Based System and Method for Control of Insulin Delivery in Diabetes Using Glucose Sensing", filed Apr. 28, 2010.
I. International Patent Application Serial No. PCT/US2008/069416, Breton, et al., entitled "Method, System and Computer Program Product for Evaluation of Insulin Sensitivity, Insulin/Carbohydrate Ratio, and Insulin Correction Factors in Diabetes from Self-Monitoring Data", filed Jul. 8, 2008, (Publication No. WO 2009/009528, Jan. 15, 2009); U.S. patent application Ser. No. 12/665,149, Breton, et al., "Method, System and Computer Program Product for Evaluation of Insulin Sensitivity, Insulin/Carbohydrate Ratio, and Insulin Correction Factors in Diabetes from Self-Monitoring Data", filed Dec. 17, 2009.
J. International Patent Application Serial No. PCT/US2008/067725, Kovatchev, et al., entitled "Method, System and Computer Simulation Environment for Testing of Monitoring and Control Strategies in Diabetes," filed Jun. 20, 2008, (Publication No. WO 2008/157781, Dec. 24, 2008); U.S. patent application Publication Ser. No. 12/664,444, Kovatchev, et al., filed Dec. 14, 2009, entitled "Method, System and Computer Simulation Environment for Testing of Monitoring and Control Strategies in Diabetes", (Publication No. 2010/0-179768, Jul. 15, 2010).
K. International Patent Application Serial No. PCT/US2008/067723, Patek, et al., entitled "LQG Artificial Pancreas Control System and Related Method", filed on Jun. 20, 2008.
L. U.S. patent application Ser. No. 12/516,044, Kovatchev, et al., filed May 22, 2009, entitled "Method, System, and Computer Program Product for the Detection of Physical Activity by Changes in Heart Rate, Assessment of Fast Changing Metabolic States, and Applications of Closed and Open Control Loop in Diabetes".
M. International Patent Application Serial No. PCT/US2007/085588, Kovatchev, et al., filed Nov. 27, 2007, entitled "Method, System, and Computer Program Product for the Detection of Physical Activity by Changes in Heart Rate, Assessment of Fast Changing Metabolic States, and Applications of Closed and Open Control Loop in Diabetes", (Publication No. WO2008/067284, Jun. 5, 2008)
N. U.S. patent application Ser. No. 11/943,226, Kovatchev, et al., filed Nov. 20, 2007, entitled "Systems, Methods and Computer Program Codes for Recognition of Patterns of Hyperglycemia and Hypoglycemia, Increased Glucose Variability, and Ineffective Self-Monitoring in Diabetes".
O. U.S. patent application Ser. No. 11/578,831, Kovatchev, et al., filed Oct. 18, 2006 entitled "Method, System and Computer Program Product for Evaluating the Accuracy of Blood Glucose Monitoring Sensors/Devices", (Publication No. US2007/0232878, Oct. 4, 2007), U.S. Pat. No. 7,815,569, Kovatchev, et al., issued Oct. 29, 2010
P. International Application Serial No. PCT/US2005/013792, Kovatchev, et al., filed Apr. 21, 2005, entitled "Method, System, and Computer Program Product for Evaluation of the Accuracy of Blood Glucose Monitoring Sensors/Devices", (Publication No. WO 05106017, Nov. 10, 2005

Q. International Patent Application Serial No. PCT/US01/09884, Kovatchev, et al., filed Mar. 29, 2001, entitled "Method, System, and Computer Program Product for Evaluation of Glycemic Control in Diabetes Self-Monitoring Data", (Publication No. WO 01/72208, Oct. 4, 2001).

R. U.S. patent application Ser. No. 10/240,228, Kovatchev, et al., filed Sep. 26, 2002, (Publication No. 0212317, Nov. 13, 2003), U.S. Pat. No. 7,025,425 B2, Kovatchev, et al., issued Apr. 11, 2006, entitled "Method, System, and Computer Program Product for the Evaluation of Glycemic Control in Diabetes from Self-Monitoring Data".

S. U.S. patent application Ser. No. 11/305,946, Kovatchev, et al., filed Dec. 19, 2005 entitled "Method, System, and Computer Program Product for the Evaluation of Glycemic Control in Diabetes from Self-Monitoring Data" (Publication No. 2006/0094947, May 4, 2006), U.S. Pat. No. 7,874,985, Kovatchev, et al., issued Jan. 25, 2011.

T. U.S. patent application Ser. No. 12/975,580, Kovatchev, et al., "Method, System, and Computer Program Product for the Evaluation of Glycemic Control in Diabetes from Self-Monitoring Data", filed Dec. 22, 2010.

U. International Patent Application Serial No. PCT/US2003/025053, Kovatchev, et al., filed Aug. 8, 2003, entitled "Method, System, and Computer Program Product for the Processing of Self-Monitoring Blood Glucose (SMBG) Data to Enhance Diabetic Self-Management", (Publication No. WO 2004/015539, Feb. 19, 2004).

V. U.S. patent application Ser. No. 10/524,094, Kovatchev, et al., filed Feb. 9, 2005 entitled "Managing and Processing Self-Monitoring Blood Glucose" (Publication No. 2005/214892, Sep. 29, 2005).

W. U.S. patent application Ser. No. 12/065,257, Kovatchev, et al., filed Aug. 29, 2008, entitled "Accuracy of Continuous Glucose Sensors", (Publication No. 2008/0314395, Dec. 25, 2008).

X. International Patent Application Serial No PCT/US2006/033724, Kovatchev, et al., filed Aug. 29, 2006, entitled "Method for Improvising Accuracy of Continuous Glucose Sensors and a Continuous Glucose Sensor Using the Same", (Publication No. WO 07027691, Mar. 8, 2007).

Y. U.S. patent application Ser. No. 12/159,891, Kovatchev, B., filed Jul. 2, 2008, entitled "Method, System and Computer Program Product for Evaluation of Blood Glucose Variability in Diabetes from Self-Monitoring Data", (Publication No. 2009/0171589, Jul. 2, 2009).

Z. International Application No. PCT/US2007/000370, Kovatchev, B., filed Jan. 5, 2007, entitled "Method, System and Computer Program Product for Evaluation of Blood Glucose Variability in Diabetes from Self-Monitoring Data", (Publication No. WO 07081853, Jul. 19, 2007).

AA. U.S. patent application Ser. No. 11/925,689 and PCT International Patent Application No. PCT/US2007/082744, Breton, et al., both filed Oct. 26, 2007, entitled "For Method, System and Computer Program Product for Real-Time Detection of Sensitivity Decline in Analyte Sensors", (Publication Nos. 2008/0172205, Jul. 17, 2008 and WO 2008/052199, May 2, 2008).

BB. U.S. patent application Ser. No. 10/069,674, Kovatchev, et al., filed Feb. 22, 2002, entitled "Method and Apparatus for Predicting the Risk of Hypoglycemia".

CC. International Application No. PCT/US00/22886, Kovatchev, et al., filed Aug. 21, 2000, entitled "Method and Apparatus for Predicting the Risk of Hypoglycemia", (Publication No. WO 01/13786, Mar. 1, 2001).

DD. U.S. Pat. No. 6,923,763 B1, Kovatchev, et al., issued Aug. 2, 2005, entitled "Method and Apparatus for Predicting the Risk of Hypoglycemia".

EE. U.S. Patent Application Publication No. US 2004/0254434 A1, "Glucose Measuring Module and "Insulin Pump Combination", published Dec. 16, 2004., Goodnow, et al. Ser. No. 10/458,914, filed Jun. 10, 2003.

FF. U.S. Patent Application Publication No. US 2009/00697456A1, Estes, et al., "Operating an Infusion Pump System", published Mar. 12, 2009. Ser. No. 11/851,194, Sep. 6, 2007.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A processor implemented method for improving the accuracy of a glucose measurement device, said method comprising:
   obtaining a glucose level readout of a subject, from said glucose measurement device;
   obtaining insulin delivery information from an insulin delivery device;
   performing a first intermediary computation using said glucose level readout from said glucose measurement device and said insulin delivery information, to obtain an output of said first intermediary computation;
   performing a second intermediary computation using said output of said first intermediary computation to obtain an output of said second intermediary computation;
   performing a third computation to reach an estimate of the blood glucose of the subject by applying a weighting scheme to said readout from the glucose measurement device and said output of said second intermediary computation; and
   determining, based at least in part on said estimate of the blood glucose of the subject, an amount of insulin to be delivered to the subject by the insulin delivery device;
   wherein the insulin delivery device is configured to deliver the determined amount of insulin to the subject.

2. The method of claim 1, wherein said glucose measurement device is a continuous glucose device.

3. The method of claim 1, wherein said first intermediary computation further comprises a Kalman Filter methodology.

4. The method of claim 1, wherein said first intermediary computation further comprises a method for filtering/state estimation using one of: an H-infinity filtering method, a Bayesian filtering method, a Monte Carlo method, and a least squares method.

5. The method of claim 1, wherein said readout from said glucose measurement device provides a periodic glucose readout.

6. The method of claim 5, wherein the frequency of said readout from said glucose measurement device is at least approximately every 60 minutes.

7. The method of claim 5, wherein the frequency of said readout from said glucose measurement device is at least approximately every 30 minutes.

8. The method of claim 5, wherein the frequency of said readout from said glucose measurement device is at least approximately every 15 minutes.

9. The method of claim 1, wherein said insulin delivery information is provided by an insulin pump, artificial pancreas, or another insulin delivery device.

10. The method of claim 1, wherein said insulin delivery information is provided by a measuring device.

11. The method of claim 1, wherein said second intermediary computation further comprises:
    inferring said output of said second intermediary computation from said output of said first intermediary computation.

12. The method of claim 11, wherein inferring said second intermediary computation further comprises:
    extrapolating said output of said first intermediary computation to some future time to determine an extrapolated state vector output.

13. The method of claim 12, wherein determining said extrapolated output is provided by $\hat{x}(t|t-\tau) = A^\tau \hat{x}(t-\tau) + A(\tau)Bu(t-\tau) + A(\tau)G\omega(t-\tau)$, wherein $\hat{x}(t|t-\tau)$ refers to the extrapolated state vector output;
   A is a state space matrix;
   B is a state space matrix;
   G is a state space matrix;
   $A^\tau = A \bullet A \bullet \bullet \bullet A$, i.e. the $\tau$-fold composition of said state space matrix A;
   $A(T) = \Sigma_{s=0}^{\tau-1} A^s$, with $A(0) = 0_{8 \times 8}$.

14. The method of claim 13, wherein said state space matrix A is:

$$A = \begin{bmatrix} .9913 & -102.7 & -1.50 \times 10^{-8} & -2.89 \times 10^{-6} & -4.1 \times 10^{-4} & 0 & 2.01 \times 10^{-6} & 4.30 \times 10^{-5} \\ 0 & .839 & 5.23 \times 10^{-10} & 7.44 \times 10^{-8} & 6.84 \times 10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9 \times 10^{-4} & .0180 & .7882 & 0 & 0 & 0 \\ .0865 & -4.667 & -2.73 \times 10^{-10} & -6.59 \times 10^{-8} & -1.26 \times 10^{-5} & .9131 & 6.00 \times 10^{-8} & 1.90 \times 10^{-6} \\ 0 & 0 & 0 & 0 & 0 & 0 & .9083 & 0 \\ 0 & 0 & 0 & 0 & 0 & 0 & .09115 & .9891 \end{bmatrix}.$$

15. The method of claim 13, wherein said state space matrix B is:

$B^T = [-3.05 \times 10^{-9}\ 1.34 \times 10^{-10}\ 0.9900\ 0.0100\ 6.50 \times 10^{-5}\ -4.61 \times 10^{-11}\ 0\ 0]$.

16. The method of claim 13, wherein said state space matrix G is:

$G^T = [6.76 \times 10^{-7}\ 0\ 0\ 0\ 0\ 1.52 \times 10^{-8}\ .9534\ 0.0464]$.

17. The method of claim 12, wherein said second intermediary computation further comprises:
    extracting a blood glucose state from said extrapolated state vector output.

18. The method of claim 17, wherein extracting said blood glucose state from said extrapolated value further comprises:
    applying a state space matrix to said extrapolated state vector output.

19. The method of claim 1, wherein said weighting scheme further comprises:
    applying a first weighting coefficient to said readout from the glucose measurement device and applying a second weighting coefficient to said output of said second intermediary computation.

20. The method of claim 19, wherein the weighting yields a linear combination of the readout from the glucose measurement device and said output of said second intermediary so that the sum of the first weighting coefficient and the second weighting coefficient is equal to 1.

21. The method of claim 19, wherein said weighting scheme further comprises:
applying more weight to said output of said second intermediary computation during hypoglycemia.

22. The method of claim 21, wherein said more weight is approximately 1.

23. The method of claim 19, wherein said weighting scheme further comprises:
applying more weight to said readout from the glucose measurement device during euglycemia.

24. The method of claim 23, wherein said more weight is approximately 1.

25. The method of claim 19, wherein said weighting scheme further comprises:
applying more weight to said readout from the glucose measurement device during hyperglycemia.

26. The method of claim 25, wherein said more weight is approximately 1.

27. The method of claim 19, wherein said weighting scheme further comprises:
applying a weighting scheme that accounted for the lack of accuracy of said output of said second intermediary computation immediately following meals and meal insulin boluses.

28. The method of claim 19, wherein said weighting scheme further comprises:
applying more weight on said readout from the glucose measurement device in the time following a detection of a large bolus of insulin.

29. The method of claim 19, wherein said weighting scheme further comprises:
basing said weighting scheme on an S-shaped curve with said curve increasing to a maximum peak value at approximately the threshold of hypoglycemia.

30. The method of claim 19, wherein said first weighting coefficient is provided by the formula $w_1 = LBGI(CGS-50)/100$ where LBGI is a low BG index and CGS is said readout from said continuous glucose measurement device.

31. A system for improving the accuracy of insulin delivery to a subject, comprising:
a glucose measurement device configured to provide a readout of a glucose level of the subject;
an insulin delivery device configured to perform insulin delivery information; and
a processor, configured to provide:
a first intermediary computation that uses said readout from said glucose measurement device of the subject and said insulin delivery information to provide an output of said first intermediary computation, and
a second intermediary computation that uses said output of said first intermediary computation to provide an output of said second intermediary computation;
wherein said processor is configured to provide a third computation to compute an estimate of the blood glucose of the subject by applying a weighting scheme to said readout from the glucose measurement device and said output of said second intermediary computation;
wherein said processor is further configured to determine, based at least in part on the estimate of the blood glucose of the subject, a determined amount of insulin to be delivered to the subject by the insulin delivery device; and
wherein said processor causes the insulin delivery device to deliver the determined amount of insulin to the subject.

32. The system of claim 31, wherein said glucose measurement device is a continuous glucose device.

33. The system of claim 31, wherein said first intermediary computation further comprises a Kalman Filter methodology.

34. The system of claim 31, wherein said first intermediary computation further comprises a method for filtering/state estimation, using one of: an H-infinity filtering method, a Bayesian filtering method, a Monte Carlo method, and a least squares method.

35. The system of claim 31, wherein said readout from said glucose measurement device provides a periodic glucose readout.

36. The system of claim 35, wherein the frequency of said readout from said glucose measurement device is at least approximately every 60 minutes.

37. The system of claim 35, wherein the frequency of said readout from said glucose measurement device is at least approximately every 30 minutes.

38. The system of claim 35, wherein the frequency of said readout from said glucose measurement device is at least approximately every 15 minutes.

39. The system of claim 31, wherein said insulin delivery information is provided by an insulin pump, artificial pancreas, or another insulin delivery device.

40. The system of claim 31, wherein said insulin delivery information is provided by a measuring device.

41. The system of claim 31, wherein said second intermediary computation further comprises:
an inference of said output of said second intermediary computation from said output of said first intermediary computation.

42. The system of claim 41, wherein inferring said second intermediary computation further comprises:
an extrapolation of said output of said first intermediary computation to some future time to determine an extrapolated state vector output.

43. The system of claim 42, wherein said extrapolated output is determined by $\hat{x}(t|t-\tau) = A^\tau \hat{x}(t-\tau) + A(\tau)Bu(t-\tau) + A(\tau)G\omega(t-\tau)$, wherein $\hat{x}(t|t-\tau)$ refers to the extrapolated state vector output;
A is a state space matrix;
B is a state space matrix;
G is a state space matrix;
$A^\tau = A \bullet A \bullet \bullet \bullet A$, i.e. the τ-fold composition of said state space matrix A;
$A(\tau) = \Sigma_{s=0}^{\tau-1} A^s$, with $A(0) = 0_{8\times 8}$.

44. The system of claim 43, wherein said state space matrix A is:

$$A = \begin{bmatrix} .9913 & -102.7 & -1.50\times 10^{-8} & -2.89\times 10^{-6} & -4.1\times 10^{-4} & 0 & 2.01\times 10^{-6} & 4.30\times 10^{-5} \\ 0 & .839 & 5.23\times 10^{-10} & 7.44\times 10^{-8} & 6.84\times 10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9\times 10^{-4} & .0180 & .7882 & 0 & 0 & 0 \\ .0865 & -4.667 & -2.73\times 10^{-10} & -6.59\times 10^{-8} & -1.26\times 10^{-5} & .9131 & 6.00\times 10^{-8} & 1.90\times 10^{-6} \\ 0 & 0 & 0 & 0 & 0 & 0 & .9083 & 0 \\ 0 & 0 & 0 & 0 & 0 & 0 & .09115 & .9891 \end{bmatrix}.$$

45. The system of claim 43, wherein said state space matrix B is:

$$B^T=[-3.05\times10^{-9}\ 1.34\times10^{-10}\ 0.9900\ 0.0100\ 6.50\times10^{-5}\ -4.61\times10^{-11}\ 0\ 0].$$

46. The system of claim 43, wherein said state space matrix G is:

$$G^T=[6.76\times10^{-7}\ 0\ 0\ 0\ 0\ 1.52\times10^{-8}\ 0.9534\ 0.0464].$$

47. The system of claim 42, wherein said second intermediary computation further comprises:
an extraction of a blood glucose state from said extrapolated state vector output.

48. The system of claim 47, wherein said extraction of said blood glucose state from said extrapolated value further comprises:
an application of a state space matrix to said extrapolated state vector output.

49. The system of claim 31, wherein said weighting scheme further comprises:
an application of a first weighting coefficient to said readout from the glucose measurement device and an application of a second weighting coefficient to said output of said second intermediary computation.

50. The system of claim 49, wherein the weighting yields a linear combination of the readout from the glucose measurement device and said output of said second intermediary so that the sum of the first weighting coefficient and the second weighting coefficient is equal to 1.

51. The system of claim 49, wherein said weighting scheme further comprises: an application of more weight to said output of said second intermediary computation during hypoglycemia.

52. The system of claim 51, wherein said more weight is approximately 1.

53. The system of claim 49, wherein said weighting scheme further comprises:
an application of more weight to said readout from the glucose measurement device during euglycemia.

54. The system of claim 53, wherein said more weight is approximately 1.

55. The system of claim 49, wherein said weighting scheme further comprises:
an application of more weight to said readout from the glucose measurement device during hyperglycemia.

56. The system of claim 55, wherein said more weight is approximately 1.

57. The system of claim 49, wherein said weighting scheme further comprises:
an application of a weighting scheme that accounted for the lack of accuracy of said output of said second intermediary computation immediately following meals and meal insulin boluses.

58. The system of claim 49, wherein said weighting scheme further comprises:
an application of more weight on said readout from the glucose measurement device in the time following a detection of a large bolus of insulin.

59. The system of claim 49, wherein said weighting scheme further comprises:
an application of said weighting scheme based on an S-shaped curve with said curve increasing to a maximum peak value at approximately the threshold of hypoglycemia.

60. The system of claim 49, wherein said first weighting coefficient is provided by the formula $w_1$=LBGI(CGS-50)/100 where LBGI is a low BG index and CGS is said readout from said continuous glucose measurement device.

61. A non-transitory computer readable storage medium having stored thereon computer readable instructions that, when executed at a computer system cause at least one processor in a computer system to:

obtain a readout of a glucose level of a subject from a glucose measurement device;
obtain insulin delivery information from an insulin delivery device;
perform a first intermediary computation using said readout from said glucose measurement device and said insulin delivery information to obtain an output of said first intermediary computation;
perform a second intermediary computation using said output of said first intermediary computation to obtain an output of said second intermediary computation;
perform a third computation to reach an estimate of the blood glucose of the subject by applying a weighting scheme to said readout from the glucose measurement device and said output of said second intermediary computation;
determine, based at least in part on the estimate of the blood glucose of the subject, a determined amount of insulin to be delivered to the subject by the insulin delivery device; and
cause the insulin delivery device to deliver the determined amount of insulin to the subject.

62. The computer program product of claim 61, wherein said glucose measurement device is a continuous glucose device.

63. The computer program product of claim 61, wherein said first intermediary computation further comprises a Kalman Filter methodology.

64. The computer program product of claim 61, wherein said first intermediary computation further comprises a method for filtering/state estimation using one of: an H-infinity filtering method, a Bayesian filtering method, a Monte Carlo method, and a least squares method.

65. The computer program product of claim 61, wherein said readout from said glucose measurement device provides a periodic glucose readout.

66. The computer program product of claim 65, wherein the frequency of said readout from said glucose measurement device is at least approximately every 60 minutes.

67. The computer program product of claim 65, wherein the frequency of said readout from said glucose measurement device is at least approximately every 30 minutes.

68. The computer program product of claim 65, wherein the frequency of said readout from said glucose measurement device is at least approximately every 15 minutes.

69. The computer program product of claim 61, wherein said insulin delivery information is provided by an insulin pump, artificial pancreas, or another insulin delivery device.

70. The computer program product of claim 61, wherein said insulin delivery information is provided by a measuring device.

71. The computer program product of claim 61, wherein said second intermediary computation further comprises: inferring said output of said second intermediary computation from said output of said first intermediary computation.

72. The computer program product of claim 71, wherein inferring said second intermediary computation further comprises: extrapolating said output of said first intermediary computation to some future time to determine an extrapolated state vector output.

73. The computer program product of claim 72, wherein determining said extrapolated output is provided by
$\hat{x}(t|t-\tau)=A^\tau \hat{x}(t-\tau)+\bar{A}(\tau)Bu(t-\tau) +\bar{A}(\tau)G\omega(t-\tau)$, wherein
$\hat{x}(t|t-\tau)$ refers to the extrapolated state vector output;
A is a state space matrix;
B is a state space matrix;
G is a state space matrix;
$A^\tau=A\bullet A\bullet\bullet\bullet A$, i.e. the $\tau$-fold composition of said state space matrix A;
$\bar{A}(\tau)=\Sigma_{s=0}^{\tau-1}A^s$, with A $(0)=0_{8\times8}$.

74. The computer program product of claim 73, wherein said state space matrix A is:

$$A = \begin{bmatrix} .9913 & -102.7 & -1.50\times10^{-8} & -2.89\times10^{-6} & -4.1\times10^{-4} & 0 & 2.01\times10^{-6} & 4.30\times10^{-5} \\ 0 & .839 & 5.23\times10^{-10} & 7.44\times10^{-8} & 6.84\times10^{-6} & 0 & 0 & 0 \\ 0 & 0 & .9798 & 0 & 0 & 0 & 0 & 0 \\ 0 & 0 & .0200 & .9798 & 0 & 0 & 0 & 0 \\ 0 & 0 & 1.9\times10^{-4} & .0180 & .7882 & 0 & 0 & 0 \\ .0865 & -4.667 & -2.73\times10^{-10} & -6.59\times10^{-8} & -1.26\times10^{-5} & .9131 & 6.00\times10^{-8} & 1.90\times10^{-6} \\ 0 & 0 & 0 & 0 & 0 & 0 & .9083 & 0 \\ 0 & 0 & 0 & 0 & 0 & 0 & .09115 & .9891 \end{bmatrix}.$$

75. The computer program product of claim 73, wherein said state space matrix B is:

$B^T = [-3.05\times10^{-9}\ 1.34\times10^{-10}\ 0.9900\ 0.0100\ 6.50\times10^{-5}\ -4.61\times10^{-11}\ 0\ 0]$.

76. The computer program product of claim 73, wherein said state space matrix G is:

$G^T = [6.76\times10^{-7}\ 0\ 0\ 0\ 0\ 1.52\times10^{-8}\ 0.9534\ 0.0464]$.

77. The computer program product of claim 72, wherein said second intermediary computation further comprises:
extracting a blood glucose state from said extrapolated state vector output.

78. The computer program product of claim 77, wherein extracting said blood glucose state from said extrapolated value further comprises:
applying a state space matrix to said extrapolated state vector output.

79. The computer program product of claim 61, wherein said weighting scheme further comprises:
applying a first weighting coefficient to said readout from the glucose measurement device and applying a second weighting coefficient to said output of said second intermediary computation.

80. The computer program product of claim 79, wherein the weighting yields a linear combination of the readout from the glucose measurement device and said output of said second intermediary so that the sum of the first weighting coefficient and the second weighting coefficient is equal to 1.

81. The computer program product of claim 79, wherein said weighting scheme further comprises:
applying more weight to said output of said second intermediary computation during hypoglycemia.

82. The computer program product of claim 81, wherein said more weight is approximately 1.

83. The computer program product of claim 79, wherein said weighting scheme further comprises:
applying more weight to said readout from the glucose measurement device during euglycemia.

84. The computer program product of claim 83, wherein said more weight is approximately 1.

85. The computer program product of claim 79, wherein said weighting scheme further comprises:
applying more weight to said readout from the glucose measurement device during hyperglycemia.

86. The computer program product of claim 85, wherein said more weight is approximately 1.

87. The computer program product of claim 79, wherein said weighting scheme further comprises:
applying a weighting scheme that accounted for the lack of accuracy of said output of said second intermediary computation immediately following meals and meal insulin boluses.

88. The computer program product of claim 79, wherein said weighting scheme further comprises:
applying more weight on said readout from the glucose measurement device in the time following a detection of a large bolus of insulin.

89. The computer program product of claim 79, wherein said weighting scheme further comprises:
basing said weighting scheme on an S-shaped curve with said curve increasing to a maximum peak value at approximately the threshold of hypoglycemia.

90. The computer program product of claim 79, wherein said first weighting coefficient is provided by the formula $w_1 = \text{LBGI}(\text{CGS}-50)/100$ where LBGI is a low BG index and CGS is said readout from said continuous glucose measurement device.

* * * * *